(12) United States Patent
Kodama et al.

(10) Patent No.: US 7,795,005 B2
(45) Date of Patent: Sep. 14, 2010

(54) BACTERIA DETECTING INSTRUMENT, BACTERIA DETECTING METHOD, AND BACTERIA DETECTING KIT

(75) Inventors: Yukiko Kodama, Takatsuki (JP); Kazushige Hatanaka, Ibaraki (JP); Kouichi Tanaka, Osaka (JP); Hiroko Nakagawa, Mino (JP); Shougo Moriya, Chiba (JP); Kaoru Osano, Chiba (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 467 days.

(21) Appl. No.: 11/065,545

(22) Filed: Feb. 25, 2005

(65) Prior Publication Data

US 2005/0272062 A1 Dec. 8, 2005

(30) Foreign Application Priority Data

Feb. 25, 2004 (JP) ............................. 2004-050523

(51) Int. Cl.
*C07H 21/02* (2006.01)
*C07H 21/04* (2006.01)
*C12M 1/34* (2006.01)
*C12Q 1/68* (2006.01)

(52) U.S. Cl. .................. 435/287.1; 536/23.1; 536/24.3

(58) Field of Classification Search .................. None
See application file for complete search history.

(56) References Cited

U.S. PATENT DOCUMENTS

| 5,908,746 A | * | 6/1999 | Suzuki et al. | .................. 435/6 |
| 2004/0219574 A1 | * | 11/2004 | Beimfohr et al. | ................. 435/6 |
| 2006/0046246 A1 | | 3/2006 | Zeng et al. | |

FOREIGN PATENT DOCUMENTS

| DE | 199 45 964 A1 | 4/2001 |
| EP | 1 063 301 A2 | 12/2000 |
| JP | 7-289295 | 11/1995 |
| JP | 2002-034571 A | 5/2002 |
| JP | 2002-034578 A | 5/2002 |
| JP | 2003-061675 A | 4/2003 |
| WO | WO02103043 A2 * | 12/2002 |

OTHER PUBLICATIONS

Wilson K.H. et al 'High-density microarray of small-subunit ribosomal DNA probes.' Appl Environ Microbiol. May 2002;68(5):2535-41.*
txid387344[orgn]—Genome Results, available from www.ncbi.nlm.nih.gov, p. 1.*
Suzuki K. et al 'Genetic characterization of non-spoilage variant isolated from beer-spoilage *Lactobacillus brevis* ABBC45.' J Appl Microbiol. 2004;96(5):946-53.*
GenBank GI:2266677 'L.lindneri 16S rRNA gene, strain LTH 2505, L40' Locus: X95423, Jul. 15, 1997, pp. 1-2.*
GenBank GI:15383733 '*Lactobacillus brevis* gene for 16S rRNA, strain:B4101' Locus: AB070606, Aug. 31, 2001, pp. 1-2.*
International Search Report mailed May 31, 2005, in International Application No. PCT/JP2005/003152.
Yasui et al., "A Specific Oligonucleotide Primer for the Rapid Detection of *Lactobacillus lindneri* by Polymerase Chain Reaction", *Can. J. Microbiol*, vol. 43, 1997, No. 2, pp. 157-163.
Priest, Fergus G., "Gram-positive Brewery Bacteria", *Brewing Microbiology*, 2003, Kluwer Acacemic/Plenum Publishers, NY, XP002538616, 2003, pp. 182-245 and 266-304.
Al-Khaldi et al., "DNA Microarray Technology Used for Studying Foodborne Pathogens and Microbial Habitats: Minireview", *Journal of AOAC International*, vol. 85, No. 4, 2002, pp. 906-910.
Rudi et al., "Protocols for 16S rDNA Array Analyses of Microbial Communities by Sequence-Specific Labeling of DNA Probes", *The Scientific World Journal*, vol. 3, 2003, pp. 578-584.
Sakamoto et al., "Beer Spoilage Bacteria and Hop Resistance", *International Journal of Food Microbiology*, vol. 89, No. 2-3, 2003, pp. 105-124.
European Search Report issued Sep. 1, 2009 in EP 05 71 0702 A1.

* cited by examiner

*Primary Examiner*—Stephen Kapushoc
(74) *Attorney, Agent, or Firm*—Drinker Biddle & Reath LLP

(57) ABSTRACT

A micro array instrument is used in which an oligonucleotide based on a species- or genus-specific nucleotide sequence of subject bacteria is immobilized on a surface of a substrate. By confirming whether the oligonucleotide immobilized on the substrate has hybridized with a probe prepared from a test sample, bacteria contained in the test sample can be detected and identified easily, quickly, and accurately.

2 Claims, 1 Drawing Sheet

FIG. 1 (a)

| | Position(Seq ID No:) | | | |
|---|---|---|---|---|
| Positive control(bacteria,control probe) | 65 | 70 | | |
| Negative control | 66 | | | |
| Genus Lactobacillus | 1 | 2 | 3 | |
| | 4 | 5 | 6 | |
| Lactobacillus brevis | 7 | 8 | 9 | 71 |
| Lactobacillus coryniformis | 10 | 11 | 12 | |
| Lactobacillus curvatus | 13 | 14 | | |
| Lactobacillus delbrueckii | 16 | 17 | 18 | |
| Lactobacillus fermentum | 19 | 20 | 21 | |
| Lactobacillus lindneri | 22 | 23 | 24 | |
| Lactobacillus malefermentans | 25 | 26 | 27 | |
| Lactobacillus casei,Lactobacillus zeae | 28 | 29 | 30 | 31 |
| Lactobacillus rhamnosus | 32 | 33 | | |
| Lactobacillus buchneri | 34 | 35 | | |
| Genus Pediococcus | 36 | 37 | 38 | |
| | 39 | 40 | 41 | |
| | 42 | 43 | 44 | 45 |
| Genus Streptococcus | 46 | 47 | | |
| Part of Genus Leuconostoc and Part of Genus Lactobacillus | 48 | 49 | 72 | |
| Genus Megasphaera | 50 | 51 | 52 | |
| | 53 | 54 | 55 | |
| Genus Pectinatus | 56 | 57 | 58 | |
| Genus Zymomonas | 59 | 60 | | |
| Enterococcus durans | 61 | 62 | | |
| Lactococcus lactis | 63 | 64 | | |

FIG. 1 (b)

Lactobacillus brevis

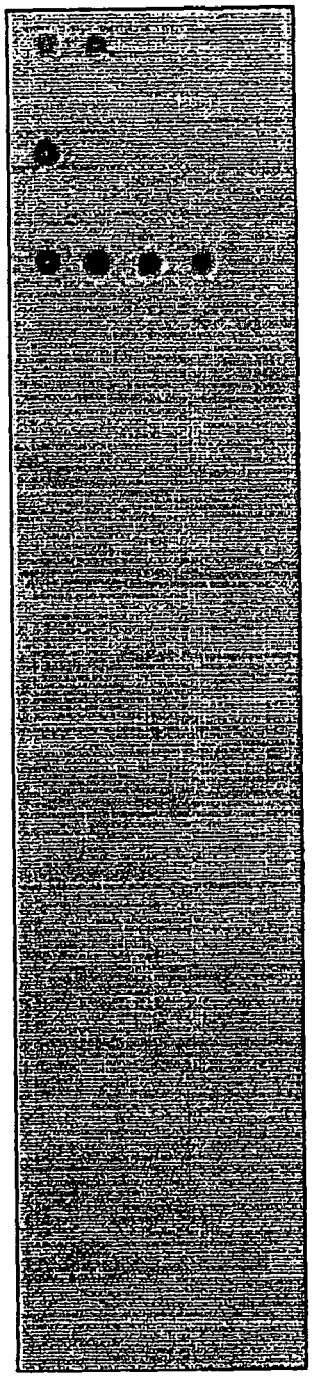

```
                             SEQUENCE LISTING

<160> NUMBER OF SEQ ID NOS: 72

<210> SEQ ID NO 1
<211> LENGTH: 13
<212> TYPE: DNA
<213> ORGANISM: Lactobacillus sp.

<400> SEQUENCE: 1
gcgaactggt gag                                                        13

<210> SEQ ID NO 2
<211> LENGTH: 16
<212> TYPE: DNA
<213> ORGANISM: Lactobacillus sp.

<400> SEQUENCE: 2
aaggcaatga tgcgta                                                     16

<210> SEQ ID NO 3
<211> LENGTH: 16
<212> TYPE: DNA
<213> ORGANISM: Lactobacillus sp.

<400> SEQUENCE: 3
aactgagagg ttgatc                                                     16

<210> SEQ ID NO 4
<211> LENGTH: 17
<212> TYPE: DNA
<213> ORGANISM: Lactobacillus sp.

<400> SEQUENCE: 4
ccttaagtgg gggataa                                                    17

<210> SEQ ID NO 5
<211> LENGTH: 16
<212> TYPE: DNA
<213> ORGANISM: Lactobacillus sp.

<400> SEQUENCE: 5
atagtaactg atcagg                                                     16

<210> SEQ ID NO 6
<211> LENGTH: 14
<212> TYPE: DNA
<213> ORGANISM: Lactobacillus sp.

<400> SEQUENCE: 6
aggcgatgat gcat                                                       14

<210> SEQ ID NO 7
<211> LENGTH: 16
<212> TYPE: DNA
<213> ORGANISM: Lactobacillus brevis

<400> SEQUENCE: 7
tgaaaggtgg cttcgg                                                     16
```

```
<210> SEQ ID NO 8
<211> LENGTH: 16
<212> TYPE: DNA
<213> ORGANISM: Lactobacillus brevis

<400> SEQUENCE: 8
taactgttca agggtt                                                    16

<210> SEQ ID NO 9
<211> LENGTH: 18
<212> TYPE: DNA
<213> ORGANISM: Lactobacillus brevis

<400> SEQUENCE: 9
taaagaagaa cacctttg                                                  18

<210> SEQ ID NO 10
<211> LENGTH: 20
<212> TYPE: DNA
<213> ORGANISM: Lactobacillus coryniformis

<400> SEQUENCE: 10
cgaagctgct tgcagtggac                                                20

<210> SEQ ID NO 11
<211> LENGTH: 15
<212> TYPE: DNA
<213> ORGANISM: Lactobacillus coryniformis

<400> SEQUENCE: 11
aacggcttac caaga                                                     15

<210> SEQ ID NO 12
<211> LENGTH: 17
<212> TYPE: DNA
<213> ORGANISM: Lactobacillus coryniformis

<400> SEQUENCE: 12
gcactgacgt cgaccga                                                   17

<210> SEQ ID NO 13
<211> LENGTH: 21
<212> TYPE: DNA
<213> ORGANISM: Lactobacillus curvatus

<400> SEQUENCE: 13
cactctcgtt agattgaaga a                                              21

<210> SEQ ID NO 14
<211> LENGTH: 17
<212> TYPE: DNA
<213> ORGANISM: Lactobacillus curvatus

<400> SEQUENCE: 14
ctgattgata acatttg                                                   17

<210> SEQ ID NO 15
<211> LENGTH: 16
<212> TYPE: DNA
<213> ORGANISM: Lactobacillus curvatus

<400> SEQUENCE: 15
gaacgtattt gatagt                                                    16
```

```
<210> SEQ ID NO 16
<211> LENGTH: 16
<212> TYPE: DNA
<213> ORGANISM: Lactobacillus delbrueckii

<400> SEQUENCE: 16
atctgcccta aagact                                                    16

<210> SEQ ID NO 17
<211> LENGTH: 17
<212> TYPE: DNA
<213> ORGANISM: Lactobacillus delbrueckii

<400> SEQUENCE: 17
actttaggat gagcccg                                                   17

<210> SEQ ID NO 18
<211> LENGTH: 16
<212> TYPE: DNA
<213> ORGANISM: Lactobacillus delbrueckii

<400> SEQUENCE: 18
cgagctgaat tcaaag                                                    16

<210> SEQ ID NO 19
<211> LENGTH: 16
<212> TYPE: DNA
<213> ORGANISM: Lactobacillus fermentum

<400> SEQUENCE: 19
ttcgcatgaa caacgc                                                    16

<210> SEQ ID NO 20
<211> LENGTH: 14
<212> TYPE: DNA
<213> ORGANISM: Lactobacillus fermentum

<400> SEQUENCE: 20
ctcgctatca cttc                                                      14

<210> SEQ ID NO 21
<211> LENGTH: 15
<212> TYPE: DNA
<213> ORGANISM: Lactobacillus fermentum

<400> SEQUENCE: 21
ttctggatgg acctg                                                     15

<210> SEQ ID NO 22
<211> LENGTH: 17
<212> TYPE: DNA
<213> ORGANISM: Lactobacillus lindneri

<400> SEQUENCE: 22
agagcaactg ctcacgg                                                   17

<210> SEQ ID NO 23
<211> LENGTH: 17
<212> TYPE: DNA
<213> ORGANISM: Lactobacillus lindneri

<400> SEQUENCE: 23
gcttgacgat agatctg                                                   17
```

```
<210> SEQ ID NO 24
<211> LENGTH: 17
<212> TYPE: DNA
<213> ORGANISM: Lactobacillus lindneri

<400> SEQUENCE: 24
gcttttatgc tatcgct                                                 17

<210> SEQ ID NO 25
<211> LENGTH: 19
<212> TYPE: DNA
<213> ORGANISM: Lactobacillus malefermentans

<400> SEQUENCE: 25
catcccgttg atttgaagt                                               19

<210> SEQ ID NO 26
<211> LENGTH: 20
<212> TYPE: DNA
<213> ORGANISM: Lactobacillus malefermentans

<400> SEQUENCE: 26
actgataatt aacatcggat                                              20

<210> SEQ ID NO 27
<211> LENGTH: 14
<212> TYPE: DNA
<213> ORGANISM: Lactobacillus malefermentans

<400> SEQUENCE: 27
ttggatagac ccgc                                                    14

<210> SEQ ID NO 28
<211> LENGTH: 17
<212> TYPE: DNA
<213> ORGANISM: Lactobacillus casei

<400> SEQUENCE: 28
cgagattcaa catggaa                                                 17

<210> SEQ ID NO 29
<211> LENGTH: 21
<212> TYPE: DNA
<213> ORGANISM: Lactobacillus casei

<400> SEQUENCE: 29
agttctcgtt gatgatcggt g                                            21

<210> SEQ ID NO 30
<211> LENGTH: 16
<212> TYPE: DNA
<213> ORGANISM: Lactobacillus casei

<400> SEQUENCE: 30
gagattcgac ttaaaa                                                  16

<210> SEQ ID NO 31
<211> LENGTH: 17
<212> TYPE: DNA
<213> ORGANISM: Lactobacillus casei

<400> SEQUENCE: 31
ttttggtcga tgaacgg                                                 17
```

```
<210> SEQ ID NO 32
<211> LENGTH: 19
<212> TYPE: DNA
<213> ORGANISM: Lactobacillus rhamnosus

<400> SEQUENCE: 32
gttctgatta ttgaaaggt                                              19

<210> SEQ ID NO 33
<211> LENGTH: 20
<212> TYPE: DNA
<213> ORGANISM: Lactobacillus rhamnosus

<400> SEQUENCE: 33
atcttgattt aattttgaac                                             20

<210> SEQ ID NO 34
<211> LENGTH: 17
<212> TYPE: DNA
<213> ORGANISM: Lactobacillus buchneri

<400> SEQUENCE: 34
cgcgtctccg ttaatga                                                17

<210> SEQ ID NO 35
<211> LENGTH: 20
<212> TYPE: DNA
<213> ORGANISM: Lactobacillus buchneri

<400> SEQUENCE: 35
aaagatttaa cattgagacg                                             20

<210> SEQ ID NO 36
<211> LENGTH: 16
<212> TYPE: DNA
<213> ORGANISM: Pediococcus sp.

<400> SEQUENCE: 36
tttagggtcg taaaac                                                 16

<210> SEQ ID NO 37
<211> LENGTH: 21
<212> TYPE: DNA
<213> ORGANISM: Pediococcus sp.

<400> SEQUENCE: 37
accgtataac agagaaaacc g                                           21

<210> SEQ ID NO 38
<211> LENGTH: 18
<212> TYPE: DNA
<213> ORGANISM: Pediococcus sp.

<400> SEQUENCE: 38
tatttggtag taactggc                                               18

<210> SEQ ID NO 39
<211> LENGTH: 21
<212> TYPE: DNA
<213> ORGANISM: Pediococcus sp.

<400> SEQUENCE: 39
gcatggaagg agattgaaag a                                           21
```

```
<210> SEQ ID NO 40
<211> LENGTH: 20
<212> TYPE: DNA
<213> ORGANISM: Pediococcus sp.

<400> SEQUENCE: 40
ttccgttaaa agaatcagaa                                               20

<210> SEQ ID NO 41
<211> LENGTH: 16
<212> TYPE: DNA
<213> ORGANISM: Pediococcus sp.

<400> SEQUENCE: 41
ctgctcatgc agtgac                                                   16

<210> SEQ ID NO 42
<211> LENGTH: 17
<212> TYPE: DNA
<213> ORGANISM: Pediococcus sp.

<400> SEQUENCE: 42
gagattttaa cacgaag                                                  17

<210> SEQ ID NO 43
<211> LENGTH: 15
<212> TYPE: DNA
<213> ORGANISM: Pediococcus sp.

<400> SEQUENCE: 43
ttgcacggaa gatga                                                    15

<210> SEQ ID NO 44
<211> LENGTH: 17
<212> TYPE: DNA
<213> ORGANISM: Pediococcus sp.

<400> SEQUENCE: 44
agtcttgacg gtatctt                                                  17

<210> SEQ ID NO 45
<211> LENGTH: 17
<212> TYPE: DNA
<213> ORGANISM: Pediococcus sp.

<400> SEQUENCE: 45
gtgcttgcac caactga                                                  17

<210> SEQ ID NO 46
<211> LENGTH: 16
<212> TYPE: DNA
<213> ORGANISM: Streptococcus sp.

<400> SEQUENCE: 46
atggacctgc gttgta                                                   16

<210> SEQ ID NO 47
<211> LENGTH: 15
<212> TYPE: DNA
<213> ORGANISM: Streptococcus sp.

<400> SEQUENCE: 47
acgcgtaggt aacct                                                    15
```

```
<210> SEQ ID NO 48
<211> LENGTH: 13
<212> TYPE: DNA
<213> ORGANISM: Leuconostoc sp.

<400> SEQUENCE: 48
gtgtgatgaa ggc                                                          13

<210> SEQ ID NO 49
<211> LENGTH: 16
<212> TYPE: DNA
<213> ORGANISM: Leuconostoc sp.

<400> SEQUENCE: 49
cggtaccata ccagaa                                                       16

<210> SEQ ID NO 50
<211> LENGTH: 18
<212> TYPE: DNA
<213> ORGANISM: Megasphaera sp.

<400> SEQUENCE: 50
aaaagatggc cactgaat                                                     18

<210> SEQ ID NO 51
<211> LENGTH: 18
<212> TYPE: DNA
<213> ORGANISM: Megasphaera sp.

<400> SEQUENCE: 51
ggaggctctt cggagctt                                                     18

<210> SEQ ID NO 52
<211> LENGTH: 19
<212> TYPE: DNA
<213> ORGANISM: Megasphaera sp.

<400> SEQUENCE: 52
ccgaaagtcg catgactgg                                                    19

<210> SEQ ID NO 53
<211> LENGTH: 17
<212> TYPE: DNA
<213> ORGANISM: Megasphaera sp.

<400> SEQUENCE: 53
tggtcaatac ccatacg                                                      17

<210> SEQ ID NO 54
<211> LENGTH: 19
<212> TYPE: DNA
<213> ORGANISM: Megasphaera sp.

<400> SEQUENCE: 54
tacccataag aagtgacgg                                                    19

<210> SEQ ID NO 55
<211> LENGTH: 16
<212> TYPE: DNA
<213> ORGANISM: Megasphaera sp.

<400> SEQUENCE: 55
cctgcccttc agatgg                                                       16
```

```
<210> SEQ ID NO 56
<211> LENGTH: 16
<212> TYPE: DNA
<213> ORGANISM: Pectinatus sp.

<400> SEQUENCE: 56
tgacggtacc ctgtta                                                    16

<210> SEQ ID NO 57
<211> LENGTH: 20
<212> TYPE: DNA
<213> ORGANISM: Pectinatus sp.

<400> SEQUENCE: 57
gtagtgttaa taccactatt                                                20

<210> SEQ ID NO 58
<211> LENGTH: 20
<212> TYPE: DNA
<213> ORGANISM: Pectinatus sp.

<400> SEQUENCE: 58
ctatagccaa taagtatagt                                                20

<210> SEQ ID NO 59
<211> LENGTH: 17
<212> TYPE: DNA
<213> ORGANISM: Zymomonas sp.

<400> SEQUENCE: 59
gaataactag gggaaac                                                   17

<210> SEQ ID NO 60
<211> LENGTH: 17
<212> TYPE: DNA
<213> ORGANISM: Zymomonas sp.

<400> SEQUENCE: 60
gagctaatac cgtatga                                                   17

<210> SEQ ID NO 61
<211> LENGTH: 18
<212> TYPE: DNA
<213> ORGANISM: Enterococcus durans

<400> SEQUENCE: 61
aaagaaaagg agtggcga                                                  18

<210> SEQ ID NO 62
<211> LENGTH: 19
<212> TYPE: DNA
<213> ORGANISM: Enterococcus durans

<400> SEQUENCE: 62
acgctttttc tttcaccgg                                                 19

<210> SEQ ID NO 63
<211> LENGTH: 18
<212> TYPE: DNA
<213> ORGANISM: Lactococcus lactis

<400> SEQUENCE: 63
aaggttggta cttgtacc                                                  18
```

```
<210> SEQ ID NO 64
<211> LENGTH: 18
<212> TYPE: DNA
<213> ORGANISM: Lactococcus lactis

<400> SEQUENCE: 64
actggatgag cagcgaac                                                 18

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence:Artificially
      Synthesized Positive Control Captuer Oligonucleotide

<400> SEQUENCE: 65
actcctacgg gaggc                                                    15

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized Negative Control Captuer Oligonucleotide

<400> SEQUENCE: 66
ctaatcggct tagcgtag                                                 18

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 67
gagtttgatc ctggctcag                                                19

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 68
gtattaccgc ggctgctg                                                 18

<210> SEQ ID NO 69
<211> LENGTH: 100
<212> TYPE: DNA
<213> ORGANISM: Artificial Sequence
<220> FEATURE:
<223> OTHER INFORMATION: Description of Artificial Sequence:Artificially
      Synthesized Control Probe Sequence

<400> SEQUENCE: 69
gagtttgatc ctggctcagg acgaacgctg gcggcatgcc tacctaatcg cgatagcgta   60
ggagccacgg ctaactacgt gccagcagcc gcggtaatac                        100
```

-continued

```
<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Positive Control Captuer Oligonucleotide

<400> SEQUENCE: 70
cctaatcgcg atagcgtagg                                               20

<210> SEQ ID NO 71
<211> LENGTH: 16
<212> TYPE: DNA
<213> ORGANISM: Lactobacillus brevis

<400> SEQUENCE: 71
gggttgacgg tattta                                                   16

<210> SEQ ID NO 72
<211> LENGTH: 15
<212> TYPE: DNA
<213> ORGANISM: Leuconostoc sp.

<400> SEQUENCE: 72
tgcatagccg agttg                                                    15
```

BACTERIA DETECTING INSTRUMENT, BACTERIA DETECTING METHOD, AND BACTERIA DETECTING KIT

This Nonprovisional application claims priority under 35 U.S.C. §119(a) on Patent Application No. 50523/2004 filed in Japan on Feb. 25, 2004, the entire contents of which are hereby incorporated by reference.

TECHNICAL FIELD

The present invention relates to bacteria detecting instruments, bacteria detecting methods, and bacteria detecting kits. Specifically, the invention relates to a bacteria detecting instrument in which bacteria-specific oligonucleotides are immobilized on a substrate surface, and to a highly accurate and user-friendly bacteria detecting method and bacteria detecting kit using such a bacteria detecting instrument.

BACKGROUND ART

Contamination of for example malt alcoholic beverages by harmful microorganisms is undesirable as it causes turbidity, off-flavor, or other adverse effects, which deteriorates product quality. Specifically, *Lactobacillus, Pediococcus,* and *Pectinatus* are some of the representative examples of harmful bacteria in beer. Among these bacteria, *Lactobacillus brevis* and *Lactobacillus lindneri* are particularly well known as beer spoilage bacteria. In a method most commonly used these days to detect such harmful bacteria, a sample of beer to be tested is filtered with a membrane filter and cultured in an appropriate medium to detect resulting colonies.

In one method of determining the identity of the colony-forming bacteria as being harmful, PCR is carried out with primers specific to the bacteria, using the extracted DNA of the colony-forming bacteria as a template, and the presence or absence of a PCR product is determined by electrophoresis (see, for example, Japanese Laid-Open Patent Publication No. 289295/1995 (Tokukaihei 7-289295; published on Nov. 7, 1995)). However, the method requires multiple rounds of PCR reactions, requiring a large number of primers for each different species of bacteria. The method therefore requires complicated procedures, and is time consuming. For shorter reaction time, the primers may be mixed together to carry out amplification in a single tube. However, since there is a limit in the number of primers that can be used, it is difficult to obtain accurate results based on a trace amount of specimen.

In order to solve these problems, there have been proposed different methods of identifying bacterial species. In these methods, primers are designed in such a manner that only a portion of a gene that commonly exists across different bacterial species and that contains species-specific sequences is amplified. After the amplification, the amplified product is excised by restriction enzymes that recognize the species-specific sequences, and bacterial species of the gene are identified based on the band size obtained by electrophoresis. However, it is not necessarily the case that such restriction enzymes are available for all species of bacteria to be tested. Further, since the methods require the highly complicated procedure of excising the amplified product with several different kinds of restriction enzymes for electrophoresis, the methods are also problematic in terms of speed and convenience.

These problems can be solved by methods employing hybridization, in which a species-specific sequence is used as a probe, and the presence or absence of a complementary sequence in the tested DNA or RNA is determined by hybridization.

However, the methods employing hybridization also pose a problem in that crosshybridization with other species often occurs between closely related species having a high level of DNA homology. As this is often the case, it is difficult to accurately identify bacterial species.

The methods having the problem of crosshybridization are particularly problematic when used for *Lactobacillus* bacteria, one of representative examples of beer spoilage bacteria, because many species of these bacteria are very closely related to one another. As such is the case, the methods cannot be used for the detection and identification of harmful bacteria.

DISCLOSURE OF INVENTION

The present invention was made in view of the foregoing problems, and an object of the invention is to provide a bacteria detecting instrument in which an oligonucleotide for accurately detecting specific bacteria is immobilized on a substrate surface. The invention also provides a bacteria detecting method and bacteria detecting kit that, with use of the bacteria detecting instrument, allow for quick and accurate detection with simple procedures.

The inventors of the present invention diligently worked to solve the foregoing problems. In achieving the object, the inventors found a genus- or species-specific nucleotide sequence in the nucleotide sequences corresponding to the 16S ribosomal RNA genes of some of the representative spoilage bacteria in malt alcoholic beverages. With an instrument in which an oligonucleotide based on such a nucleotide sequence is immobilized on a substrate surface, quick and accurate detection and identification of bacteria was possible through hybridization with the nucleic acid derived from the test sample.

Namely, the present invention provides an instrument for detecting and identifying bacteria contained in a test sample, wherein: subject bacteria are at least two kinds of bacteria selected from the group consisting of: (1) *Lactobacillus brevis*; (2) *Lactobacillus lindneri*; (3) *Pediococcus*; (4) *Megasphaera*; and (5) *Pectinatus*; and the instrument includes a substrate on a surface of which an oligonucleotide based on a species- or genus-specific nucleotide sequence of the subject bacteria is immobilized, and the bacteria contained in the test sample are detected and identified through hybridization of the oligonucleotide with a nucleic acid derived from the test sample.

Among the bacteria (1) through (5) of the present invention, *Lactobacillus brevis* includes all of the nucleotide sequences of SEQ ID NOs: 7 through 9, and 71 in the 16S ribosomal RNA gene, for example. In *Lactobacillus lindneri*, all of the nucleotide sequences of SEQ ID NOs: 22 through 24 are included in the 16S ribosomal RNA gene. In *Pediococcus*, at least two of the nucleotide sequences of SEQ ID NOs: 36 through 45 are included in the 16S ribosomal RNA gene. In *Megasphaera*, at least two of the nucleotide sequences of SEQ ID NOs: 50 through 55 are included in the 16S ribosomal RNA gene. In *Pectinatus*, at least two of the nucleotide sequences of SEQ ID NOs: 56 through 58 are included in the 16S ribosomal RNA gene.

In the bacteria detecting instrument of the present invention, it is preferable that the subject bacteria include: (6) *Lactobacillus*; (7) *Streptococcus*; (8) *Leuconostoc*; (9) *Zymomonas*; (10) *Lactobacillus coryniformis*; (11) *Lactobacillus curvatus*; (12) *Lactobacillus delbrueckii*; (13) *Lactobacillus fermentum*; (14) *Lactobacillus malefermentans*; (15) a *Lactobacillus casei* species group (*Lactobacillus casei, Lactobacillus paracasei, Lactobacillus zeae*); (16) *Lactoba-* cillus rhamnosus; (17) Lactobacillus buchneri; (18) Enterococcus durans; and (19) Lactococcus lactis.

The oligonucleotide immobilized on the substrate surface is preferably selected from a group of oligonucleotides set forth below. In a bacteria detecting instrument of the present invention, at least one of the following oligonucleotides is immobilized on a substrate surface.

(A) Oligonucleotides based on a genus-specific sequence of nucleotide sequences corresponding to a 16S ribosomal RNA gene of Lactobacillus, including: an oligonucleotide including a nucleotide sequence of SEQ ID NO: 1; an oligonucleotide including a nucleotide sequence of SEQ ID NO: 2; an oligonucleotide including a nucleotide sequence of SEQ ID NO: 3; an oligonucleotide including a nucleotide sequence of SEQ ID NO: 4; an oligonucleotide including a nucleotide sequence of SEQ ID NO: 5; and an oligonucleotide including a nucleotide sequence of SEQ ID NO: 6.

(B) Oligonucleotides based on a species-specific sequence of nucleotide sequences corresponding to a 16S ribosomal RNA gene of Lactobacillus brevis, including: an oligonucleotide including a nucleotide sequence of SEQ ID NO: 7; an oligonucleotide including a nucleotide sequence of SEQ ID NO: 8; an oligonucleotide including a nucleotide sequence of SEQ ID NO: 9; and an oligonucleotide including a nucleotide sequence of SEQ ID NO: 71.

(C) Oligonucleotides based on a species-specific sequence of nucleotide sequences corresponding to a 16S ribosomal RNA gene of Lactobacillus coryniformis, including: an oligonucleotide including a nucleotide sequence of SEQ ID NO: 10; an oligonucleotide including a nucleotide sequence of SEQ ID NO: 11; and an oligonucleotide including a nucleotide sequence of SEQ ID NO: 12.

(D) Oligonucleotides based on a species-specific sequence of nucleotide sequences corresponding to a 16S ribosomal RNA gene of Lactobacillus curvatus, including: an oligonucleotide including a nucleotide sequence of SEQ ID NO: 13; and an oligonucleotide including a nucleotide sequence of SEQ ID NO: 14.

(E) Oligonucleotides based on a species-specific sequence of nucleotide sequences corresponding to a 16S ribosomal RNA gene of Lactobacillus delbrueckii, including: an oligonucleotide including a nucleotide sequence of SEQ ID NO: 16; an oligonucleotide including a nucleotide sequence of SEQ ID NO: 17; and an oligonucleotide including a nucleotide sequence of SEQ ID NO: 18.

(F) Oligonucleotides based on a species-specific sequence of nucleotide sequences corresponding to a 16S ribosomal RNA gene of Lactobacillus fermentum, including: an oligonucleotide including a nucleotide sequence of SEQ ID NO: 19; an oligonucleotide including a nucleotide sequence of SEQ ID NO: 20; and an oligonucleotide including a nucleotide sequence of SEQ ID NO: 21.

(G) Oligonucleotides based on a species-specific sequence of nucleotide sequences corresponding to a 16S ribosomal RNA gene of Lactobacillus lindneri, including: an oligonucleotide including a nucleotide sequence of SEQ ID NO: 22; an oligonucleotide including a nucleotide sequence of SEQ ID NO: 23; and an oligonucleotide including a nucleotide sequence of SEQ ID NO: 24.

(H) Oligonucleotides based on a species-specific sequence of nucleotide sequences corresponding to a 16S ribosomal RNA gene of Lactobacillus malefermentans, including: an oligonucleotide including a nucleotide sequence of SEQ ID NO: 25; an oligonucleotide including a nucleotide sequence of SEQ ID NO: 26; and an oligonucleotide including a nucleotide sequence of SEQ ID NO: 27.

(I) Oligonucleotides based on a species-specific sequence of nucleotide sequences corresponding to a 16S ribosomal RNA gene of a Lactobacillus casei species group (Lactobacillus casei, Lactobacillus paracasei, Lactobacillus zeae), including: an oligonucleotide based on a sequence specific to Lactobacillus casei (Lactobacillus paracasei), wherein the oligonucleotide includes a nucleotide sequence of SEQ ID NO: 28, and wherein the oligonucleotide includes a nucleotide sequence of SEQ ID NO: 29; and an oligonucleotide based on a sequence specific to Lactobacillus zeae (including a type strain of Lactobacillus casei), wherein the oligonucleotide includes a nucleotide sequence of SEQ ID NO: 30, and wherein the oligonucleotide includes a nucleotide sequence of SEQ ID NO: 31.

(J) Oligonucleotides based on a species-specific sequence of nucleotide sequences corresponding to a 16S ribosomal RNA gene of Lactobacillus rhamnosus, including: an oligonucleotide including a nucleotide sequence of SEQ ID NO: 32; and an oligonucleotide including a nucleotide sequence of SEQ ID NO: 33.

(K) Oligonucleotides based on a species-specific sequence of nucleotide sequences corresponding to a 16S ribosomal RNA gene of Lactobacillus buchneri, including: an oligonucleotide including a nucleotide sequence of SEQ ID NO: 34; and an oligonucleotide including a nucleotide sequence of SEQ ID NO: 35.

(L) Oligonucleotides based on a genus-specific sequence of nucleotide sequences corresponding to a 16S ribosomal RNA gene of Pediococcus, including: an oligonucleotide including a nucleotide sequence of SEQ ID NO: 36; an oligonucleotide including a nucleotide sequence of SEQ ID NO: 37; an oligonucleotide including a nucleotide sequence of SEQ ID NO: 38; an oligonucleotide including a nucleotide sequence of SEQ ID NO: 39; an oligonucleotide including a nucleotide sequence of SEQ ID NO: 40; an oligonucleotide including a nucleotide sequence of SEQ ID NO: 41; an oligonucleotide including a nucleotide sequence of SEQ ID NO: 42; an oligonucleotide including a nucleotide sequence of SEQ ID NO: 43; an oligonucleotide including a nucleotide sequence of SEQ ID NO: 44; and an oligonucleotide including a nucleotide sequence of SEQ ID NO: 45.

(M) Oligonucleotides based on a genus-specific sequence of nucleotide sequences corresponding to a 16S ribosomal RNA gene of Streptococcus, including: an oligonucleotide including a nucleotide sequence of SEQ ID NO: 46; and an oligonucleotide including a nucleotide sequence of SEQ ID NO: 47.

(N) Oligonucleotides based on a genus-specific sequence of nucleotide sequences corresponding to a 16S ribosomal RNA gene of Leuconostoc, including: an oligonucleotide including a nucleotide sequence of SEQ ID NO: 48; and an oligonucleotide including a nucleotide sequence of SEQ ID NO: 49.

(O) Oligonucleotides based on a genus-specific sequence of nucleotide sequences corresponding to a 16S ribosomal RNA gene of Megasphaera, including: an oligonucleotide including a nucleotide sequence of SEQ ID NO: 50; an oligonucleotide including a nucleotide sequence of SEQ ID NO: 51; an oligonucleotide including a nucleotide sequence of SEQ ID NO: 52; an oligonucleotide including a nucleotide sequence of SEQ ID NO: 53; an oligonucleotide including a nucleotide sequence of SEQ ID NO: 54; and an oligonucleotide including a nucleotide sequence of SEQ ID NO: 55.

(P) Oligonucleotides based on a genus-specific sequence of nucleotide sequences corresponding to a 16S ribosomal RNA gene of Pectinatus, including: an oligonucleotide including a nucleotide sequence of SEQ ID NO: 56; an oligonucleotide including a nucleotide sequence of SEQ ID NO: 57; and an oligonucleotide including a nucleotide sequence of SEQ ID NO: 58.

(Q) Oligonucleotides based on a genus-specific sequence of nucleotide sequences corresponding to a 16S ribosomal RNA gene of *Zymomonas*, including: an oligonucleotide including a nucleotide sequence of SEQ ID NO: 59; and an oligonucleotide including a nucleotide sequence of SEQ ID NO: 60.

(R) Oligonucleotides based on a species-specific sequence of nucleotide sequences corresponding to a 16S ribosomal RNA gene of *Enterococcus durans*, including: an oligonucleotide including a nucleotide sequence of SEQ ID NO: 61; and an oligonucleotide including a nucleotide sequence of SEQ ID NO: 62.

(S) Oligonucleotides based on a species-specific sequence of nucleotide sequences corresponding to a 16S ribosomal RNA gene of *Lactococcus lactis*, including: an oligonucleotide including a nucleotide sequence of SEQ ID NO: 63; and an oligonucleotide including a nucleotide sequence of SEQ ID NO: 64.

(T) An oligonucleotide including a nucleotide sequence of SEQ ID NO: 72 from among common nucleotide sequences corresponding to a 16S ribosomal RNA gene of some *Leuconostoc* and some *Lactobacillus*.

With a bacteria detecting instrument immobilizing the bacteria of (A) through (T) on a substrate surface, spoilage bacteria in food and particularly malt alcoholic beverages can be detected and identified thoroughly.

It is preferable in the bacteria detecting instrument of the present invention that the substrate has a carbodiimide group or isocyanate group which reacts and forms a covalent bond with the oligonucleotide or a linker attached to an end of the oligonucleotide.

The present invention provides a bacteria detecting method for detecting and identifying bacteria contained in a test sample, the method including: a nucleic acid preparing step of preparing a nucleic acid of the bacteria contained in the test sample; a probe preparing step of preparing a labeling probe, using the nucleic acid as a template; a hybridization step of causing the labeling probe to hybridize with an oligonucleotide immobilized on a surface of a substrate; and a signal detecting step of detecting a hybridization signal.

In the bacteria detecting method of the present invention, the test sample is preferably food, and most preferably a malt alcoholic beverage.

A bacteria detecting kit according to the present invention is for carrying out the bacteria detecting method, and includes the bacteria detecting instrument. It is preferable that the bacteria detecting kit include reagents used in the hybridization step, signal detecting step, probe preparing step, and nucleic acid preparing step.

For a fuller understanding of the nature and advantages of the invention, reference should be made to the ensuing detailed description taken in conjunction with the accompanying drawings.

BRIEF DESCRIPTION OF DRAWINGS

FIG. 1(*a*) represents positions of oligonucleotides immobilized on a substrate of a bacteria detecting instrument according to the present invention, as used in Examples.

FIG. 1(*b*) represents an image showing a detection result for *Lactobacillus brevis*, obtained with the bacteria detecting instrument immobilizing the oligonucleotides at positions shown in FIG. 1(*a*).

BEST MODE FOR CARRYING OUT THE INVENTION (1) Bacteria Detecting Instrument According to the Present Invention A bacteria detecting instrument according to the present invention is for detecting and identifying bacteria contained in a test sample. The bacteria detecting instrument includes a substrate on which an oligonucleotide based on a species- or genus-specific nucleotide sequence of subject bacteria is immobilized. Detection and identification of bacteria in the test sample is enabled by hybridization of the oligonucleotide with the nucleic acid derived from the test sample.

[Substrate]

For a substrate used in a bacteria detecting instrument according to the present invention, materials that can stably immobilize oligonucleotides are used. Non-limiting examples of such materials include synthetic resins, such as polycarbonate or plastic, and glass. A shape of the substrate is not particularly limited either. For example, a board substrate or film substrate can be suitably used.

[Oligonucleotides Immobilized on a Substrate Surface]

Oligonucleotides immobilized on a substrate surface of a bacteria detecting instrument according to the present invention are based on nucleotide sequences specific to the species or genus to which the subject bacteria belong. A particular species or genus of bacteria contained in a test sample can be detected if the oligonucleotides hybridize with the nucleic acid derived from the test sample. As used herein, oligonucleotides based on species- or genus-specific nucleotide sequences of subject bacteria will be referred to as "capture oligonucleotides."

The species- or genus-specific nucleotide sequence may be found in the nucleotide sequences in the genome of the subject bacteria, or more preferably in the nucleotide sequences corresponding to the 16S ribosomal RNA gene of the subject bacteria. The 16S ribosomal RNA gene of bacteria is known to contain a large number of species- or genus-specific nucleotide sequences. It is therefore particularly preferable that the species- or genus-specific nucleotide sequence be found in the DNA sequences corresponding to the 16S ribosomal RNA gene. The nucleotide sequences of the ribosomal RNA gene are available from sources such as the GenBank, EMBL, DDBJ, or other databases.

The capture oligonucleotides are designed based on the species- or genus-specific nucleotide sequences. As such, the capture oligonucleotides may be the species- or genus-specific nucleotide sequences themselves, or may include a mutation wherever across the sequences as long as they can specifically hybridize with the nucleic acid obtained from the subject bacteria.

The length (the number of bases) of the capture oligonucleotide is not particularly limited. However, detection of hybridization becomes difficult when it is too short. When it is too long, non-specific hybridization may result. After a series of analyses on optimum length of capture oligonucleotide, the inventors determined that the optimum length was typically 12 to 24 base long, or more preferably 13 to 22 base long. However, the length of capture oligonucleotide is not just limited to these. The inventors have confirmed that the base length is largely dependent on the sequence profile (a proportion of a specific base, the number of repeats of a specific base), and that even a short chain allows for specific hybridization if it possesses a good bonding capacity.

In the case where the capture oligonucleotide has a steric structure such as a hairpin structure or loop structure, hybridization with the nucleic acid derived from the test sample may not be achieved. Such a steric structure can be broken by replacing one or more nucleotides of the capture oligonucleotide with inosine or a nucleic acid that does not form paring with any nucleotide.

A synthesis method of capture oligonucleotides is not particularly limited. For example, a method described in Maniatis, T. et al., Molecular Cloning A Laboratory Manual, Second Edition, Cold Spring Harbor Laboratory Press (1989) may be used. Generally, the capture oligonucleotides are synthesized using a commercially available DNA synthesizer.

In a bacteria detecting instrument according to the present invention, it is preferable that so-called control capture oligonucleotides be immobilized on the substrate surface, in addition to the oligonucleotides based on the species- or genus-specific nucleotide sequences of the subject bacteria. The control capture oligonucleotides include positive control capture oligonucleotides and negative control capture oligonucleotides. The positive control capture oligonucleotides are used to check the amplification reaction carried out in a probe preparing step to be described later. The negative control capture oligonucleotides are used to check for non-specific hybridization, i.e., a false-positive hybridization signal. Therefore, the present invention also includes a bacteria detecting instrument in which the positive control capture oligonucleotides and negative control capture oligonucleotides are immobilized on a substrate surface.

The positive control capture oligonucleotide may be designed based on a nucleotide sequence contained in the probe prepared from subject bacteria. In the case where different subject bacteria are detected using a single bacteria detecting instrument, the positive control capture oligonucleotide may be designed for each subject, or based on a common nucleotide sequence of the probes prepared from different subjects. In the case where the probes prepared from different subject bacteria do not have a common nucleotide sequence, the positive control capture oligonucleotide may be designed for each group of the subject bacteria. Alternatively, a synthetic sequence may be designed that differs from the sequence of the subject bacteria except for the primer sequence, and part of this sequence may be used as the positive control capture oligonucleotide. By using such a synthetic sequence as a template, a probe may be prepared ("control probe" in the invention), and the resulting probe may be added to a probe prepared from the test sample. In this way, the specificity of hybridization can be determined. The probes will be described later in more detail.

It is preferable that the negative control capture oligonucleotide be designed such that it has a nucleotide sequence of a positive control capture oligonucleotide with the forced substitution of one or more bases but less than 20% of the total bases of the sequence. The number of substituted bases is decided taking into consideration hybridization condition, so that the negative control capture oligonucleotide does not hybridize with the probes derived from the subject bacteria.

The subject bacteria are not particularly limited, and are suitably selected from those contained in a test sample. For example, bacteria that are likely to contaminate and spoil foods can be selected as subject bacteria. Particularly preferable are those that are likely to contaminate and spoil malt alcoholic beverages. Contamination of food by harmful bacteria is a big concern for public health. In malt alcoholic beverages as represented by beer and low-malt beer, contamination by harmful bacteria deteriorates product quality by causing turbidity, off-flavor, or other undesirable effects. Therefore, there is a strong demand for a method that allows for quick and accurate detection and identification of harmful bacteria.

Examples of spoilage bacteria in malt alcoholic beverages include those belonging to genus *Lactobacillus, Pediococcus, Streptococcus, Megasphera*, and *Pectinatus*. Examples of species that belong to genus *Lactobacillus* include *Lactobacillus brevis, Lactobacillus coryniformis, Lactobacillus curvatus, Lactobacillus delbrueckii, Lactobacillus fermentum, Lactobacillus lindneri, Lactobacillus malefermentans, Lactobacillus casei* (*Lactobacillus paracasei*), *Lactobacillus rhamnosus, Lactobacillus buchneri*, and *Lactobacillus zeae* (including a type strain of *Lactobacillus casei*). Other food spoilage bacteria include those belonging to genus *Leuconostoc* and *Zymomonas*, and species *Enterococcus durans* and *Lactococcus lactis*. However, the subject bacteria are not just limited to these.

The capture oligonucleotides for detecting and identifying bacteria as exemplified above are, for example, oligonucleotides based on genus-specific nucleotide sequences corresponding to the 16S ribosomal RNA genes of bacteria that belong to genus *Lactobacillus, Pediococcus, Streptococcus, Leuconostoc, Megasphaera, Pectinatus*, and *Zymomonas*. As another example, the capture oligonucleotides may be oligonucleotides based on species-specific nucleotide sequences corresponding to the 16S ribosomal RNA genes of *Lactobacillus brevis, Lactobacillus coryniformis, Lactobacillus curvatus, Lactobacillus delbrueckii, Lactobacillus fermentum, Lactobacillus lindneri, Lactobacillus malefermentans, Lactobacillus casei* (*Lactobacillus paracasei*), *Lactobacillus rhamnosus, Lactobacillus buchneri, Lactobacillus zeae* (including a type strain of *Lactobacillus casei*), *Enterococcus durans*, and *Lactococcus lactis*. More specifically, the capture oligonucleotides may be but not limited to oligonucleotides having the nucleotide sequences of SEQ ID NOs: 1 through 64, and 71 and 72.

Table 1 below lists examples of *Lactobacillus* bacteria that are detectable by the capture oligonucleotides (SEQ ID NOs: 1 through 6) that are based on nucleotide sequences specific to genus *Lactobacillus*, and the capture oligonucleotide (SEQ ID NO: 72) based on a nucleotide sequence corresponding to part of the *Lactobacillus* bacteria and part of the *Leuconostoc* bacteria. It should be noted here that the bacteria that are detectable by the capture oligonucleotides of the nucleotide sequences of SEQ ID NO: 1 through 6, and 72 are not just limited to these bacteria.

TABLE 1

*Lactobacillus acetotolerans*
*Lactobacillus acidifarinae*
*Lactobacillus acidipiscis*
*Lactobacillus acidophilus*
*Lactobacillus agilis*
*Lactobacillus amylolyticus*
*Lactobacillus amylovorus*
*Lactobacillus animalis*
*Lactobacillus antri*
*Lactobacillus arizonensis*
*Lactobacillus brevis*
*Lactobacillus buchneri*
*Lactobacillus casei*
*Lactobacillus collinoides*
*Lactobacillus coryniformis*
*Lactobacillus crispatus*
*Lactobacillus curvatus*
*Lactobacillus delbrueckii*
*Lactobacillus diolivorans*
*Lactobacillus durianis*
*Lactobacillus ensenii*
*Lactobacillus equi*
*Lactobacillus ferintoshensis*
*Lactobacillus fermentum*
*Lactobacillus fructivorans*

TABLE 1-continued

Lactobacillus frumenti
Lactobacillus fuchuensis
Lactobacillus gallinarum
Lactobacillus gasseri
Lactobacillus hamsteri
Lactobacillus helveticus
Lactobacillus hilgardii
Lactobacillus iners
Lactobacillus intestinalis
Lactobacillus johnsonii
Lactobacillus kalixensis
Lactobacillus kefiranofaciens
Lactobacillus kefiri
Lactobacillus kitasatonis
Lactobacillus kunkeei
Lactobacillus lindneri
Lactobacillus malefermentans
Lactobacillus murinus
Lactobacillus nagelii
Lactobacillus oris
Lactobacillus panis
Lactobacillus pantheris
Lactobacillus parabuchneri
Lactobacillus paracasei
Lactobacillus parakefiri
Lactobacillus paraplantarum
Lactobacillus pentosus
Lactobacillus plantarum
Lactobacillus pontis
Lactobacillus psittaci
Lactobacillus reuteri
Lactobacillus rhamnosus
Lactobacillus ruminis
Lactobacillus sakei
Lactobacillus salicinius
Lactobacillus salivarius
Lactobacillus sanfranciscensis
Lactobacillus sharpeae
Lactobacillus suebicus
Lactobacillus suntoryeus
Lactobacillus tolerans
Lactobacillus ultunensis
Lactobacillus vaccinostercus
Lactobacillus vaginalis
Lactobacillus zeae
Lactobacillus zymae Table 2 below lists examples of bacteria that are detectable by the capture oligonucleotides (SEQ ID NOs: 36 through 45) that are based on nucleotide sequences specific to *Pediococcus*. It should be noted here that the bacteria that are detectable by the capture oligonucleotides having the nucleotide sequences of SEQ ID NOs: 36 through 45 are not just limited to these bacteria.

TABLE 2

Pediococcus acidilactici
Pediococcus pentosaceus
Pediococcus damnosus
Pediococcus inopinatus
Pediococcus parvulus
Pediococcus claussenii
Pediococcus dextrinicus
Pediococcus urinaeequi Table 3 below lists examples of bacteria that are detectable by the capture oligonucleotides (SEQ ID NOs: 46 and 47) that are based on nucleotide sequences specific to *Streptococcus*. It should be noted here that the bacteria that are detectable by the capture oligonucleotides having the nucleotide sequences of SEQ ID NOs: 46 and 47 are not just limited to these bacteria.

TABLE 3

| | |
|---|---|
| Streptococcus alactolyticus | Streptococcus anginosus |
| Streptococcus macedonicus | Streptococcus sinensis |
| Streptococcus bovis | Streptococcus downei |
| Streptococcus equinus | Streptococcus ferus |
| Streptococcus infantarius | Streptococcus oralis |
| Streptococcus lutetiensis | Streptococcus parasanguinis |
| Streptococcus gallolyticus | Streptococcus cristatus |
| Streptococcus acidominimus | Streptococcus gordonii |
| Streptococcus canis | Streptococcus infantis |
| Streptococcus dysgalactiae | Streptococcus mitis |
| Streptococcus equisimilis | Streptococcus pneumoniae |
| Streptococcus iniae | Streptococcus ovis |
| Streptococcus parauberis | Streptococcus peroris |
| Streptococcus porcinus | Streptococcus pluranimalium |
| Streptococcus pyogenes | Streptococcus ratti |
| Streptococcus urinalis | Streptococcus mutans |
| Streptococcus agalactiae | Streptococcus thoraltensis |
| Streptococcus criceti | Streptococcus entericus |
| Streptococcus didelphis | Streptococcus salivarius |
| Streptococcus zooepidemicus | Streptococcus thermophilus |
| Streptococcus equi | Streptococcus sobrinus |
| Streptococcus gallinaceus | Streptococcus australis |
| Streptococcus suis | Streptococcus macacae |
| Streptococcus hyointestinalis | Streptococcus orisratti |
| Streptococcus intermedius | Streptococcus phocae |
| Streptococcus constellatus | Streptococcus difficilis |

Table 4 below lists examples of *Leuconostoc* bacteria that are detectable by the capture oligonucleotides (SEQ ID NOs: 48 and 49) that are based on nucleotide sequences specific to *Leuconostoc*, and the capture oligonucleotide (SEQ ID NO: 72) that is based on a nucleotide sequence corresponding to part of the *Lactobacillus* bacteria and part of the *Leuconostoc* bacteria. It should be noted here that the bacteria that are detectable by the capture oligonucleotides having the nucleotide sequences of SEQ ID NOs: 48, 49, and 72 are not just limited to these bacteria.

TABLE 4

Leuconostoc argentinum
Leuconostoc carnosum
Leuconostoc citreum
Leuconostoc cremoris
Leuconostoc dextranicum
Leuconostoc fallax
Leuconostoc ficulneum
Leuconostoc fructosum
Leuconostoc garlicum
Leuconostoc gasicomitatum
Leuconostoc gelidum
Leuconostoc inhae
Leuconostoc kimchii
Leuconostoc lactis
Leuconostoc mesenteroides
Leuconostoc pseudoficulneum
Leuconostoc pseudomesenteroides Examples of bacteria that are detectable by the capture oligonucleotides (SEQ ID NOs: 50 through 55) that are based on nucleotide sequences specific to *Megasphera* include *Megasphaera cerevisiae*, *Megasphaera elsdenii*, and *Megasphaera micronuciformis*. It should be noted here that the bacteria that are detectable by the capture oligonucleotides having the nucleotide sequences of SEQ ID NOs: 50 through 55 are not just limited to these bacteria.

Examples of bacteria that are detectable by the capture oligonucleotides (SEQ ID NOs: 56 through 58) that are based on nucleotide sequences specific to *Pectinatus* include *Pectinatus cerevisiiphilus* and *Pectinatus frisingensis*. It should be noted here that the bacteria that are detectable by the capture oligonucleotides having the nucleotide sequences of SEQ ID NOs: 56 through 58 are not just limited to these bacteria.

Examples of bacteria that are detectable by the capture oligonucleotides (SEQ ID NOs: 59 and 60) that are based on nucleotide sequences specific to *Zymomonas* include *Zymomonas mobilis* and *Zymomonas pomaceae*. It should be noted here that the bacteria that are detectable by the capture oligonucleotides having the nucleotide sequences of SEQ ID NOs: 59 and 60 are not just limited to these bacteria.

The capture oligonucleotide immobilized on a substrate surface of a bacteria detecting instrument according to the present invention is not particularly limited as long as it can hybridizes with a probe prepared from subject bacteria. As such, the oligonucleotides having the nucleotide sequences of SEQ ID NOs: 1 through 64, 71 and 72 may include only the nucleotide sequences of SEQ ID NOs: 1 through 64, 71 and 72, or sequences other than these sequences. Such a capture oligonucleotide including a sequence other than the nucleotide sequences of SEQ ID NOs: 1 through 64, 71 and 72 may be an oligonucleotide prepared by elongating the 3' end or 5' end, or both ends of each nucleotide sequence of SEQ ID NOs: 1 through 64, 71 and 72 based on a nucleotide sequence of the 16S ribosomal RNA gene. The present invention also includes a bacteria detecting instrument in which such an oligonucleotide is immobilized on a substrate surface.

On the substrate, at least one kind of capture oligonucleotide is immobilized. However, more than one kind of capture oligonucleotide may be immobilized in any number. However, for procedural convenience and shorter test time for the detection of contaminating bacteria in a sample, it would be preferable if detectable bacteria in the sample were detected altogether with the use of a single substrate. Thus, a bacteria detecting instrument according to the present invention can be used most preferably if it is a so-called micro-array instrument, in which more than one capture oligonucleotide corresponding to different target species or genus of bacteria is immobilized on a single substrate. For example, when the test sample is a malt alcoholic beverage, it is preferable that the capture oligonucleotides immobilized on a substrate surface correspond to bacteria that belong to genus *Lactobacillus, Pediococcus, Streptococcus, Leuconostoc, Megasphaera, Pectinatus*, and *Zymomonas*.

[Immobilization of Oligonucleotides (Capture Oligonucleotides)]

A method of immobilizing the oligonucleotides on a substrate surface is not particularly limited and may be suitably selected from known methods. For example, a method employed in common hybridization methods such as physical absorption, electron bonding, or molecular covalent bonding can be used. In a bacteria detecting instrument according to the present invention, it is preferable that the oligonucleotides be immobilized using a substrate on which a carbodiimido group or isocyanate group is attached (U.S. Pat. No. 5,908,746, Japanese Laid-Open Patent Publication No. 23975/1996 (Tokukaihei 8-23975)).

In spotting the oligonucleotides, insufficient spotting may cause errors as the level of reactivity between the oligonucleotides and probes becomes poor. As for high-density spotting, the technique is associated with technical problems and is costly. Further, it requires a detecting device (for example, scanner) that requires more precision and is more expensive than that required for the detection of hybridization signals using fluorescence labeling or chemical luminescence for the probes. It is therefore preferable that the oligonucleotides be immobilized on a substrate surface within a diameter of 10 μm to 1,000 μm. A method of spotting the oligonucleotides on the substrate surface is not particularly limited. For example, a solution of oligonucleotide may be spotted on the substrate surface using a spotting machine. In this case, the oligonucleotide solution generally forms substantially circular spots.

(2) A Bacteria Detecting Method According to the Present Invention

A bacteria detecting method according to the present invention is for detecting and identifying bacteria contained in a test sample, and includes: a nucleic acid preparing step of preparing a nucleic acid of bacteria contained in a test sample; a probe preparing step of preparing a labeling probe, using the nucleic acid as a template; a hybridization step of hybridizing the labeling probe with an oligonucleotide that is based on a species- or genus-specific sequence of subject bacteria; and a signal detecting step of detecting a hybridization signal. In the hybridization step of the bacteria detecting method, it is preferable to use a bacteria detecting instrument according to the present invention. The bacteria detecting instrument allows for thorough detection and identification that is more convenient, faster, and more accurate. A test sample used in a bacteria detecting method of the present invention is preferably food, and malt alcoholic beverages are particularly preferable. The following will describe each step in more detail.

[Nucleic Acid Preparing Step]

In the nucleic acid preparing step, the nucleic acid of the bacteria contained in a test sample is prepared. A preparation method of a nucleic acid in the test sample can be suitably selected from known nucleic acid preparation methods. For example, for the preparation of DNA, a method described in R-F. Wang, Molecular and Cellular Probes (2000) 14, 1-5 may be used for the extraction. Other than such typical preparation methods, any of many alternative methods may be used as well. Further, a commercially available kit may also be used.

[Probe Preparing Step]

In the probe preparing step, a labeling probe is prepared using a template, for which the nucleic acid prepared in the nucleic acid preparing step is used. The probe is prepared, for example, by amplifying the nucleic acid, using a primer that is designed to include nucleotide sequences of the capture oligonucleotide and positive control capture oligonucleotide. An amplification method of nucleic acid is not particularly limited. For example, DNA may be amplified by PCR, or an in vitro transcription method may be used to amplify RNA.

For example, in the case where a labeling probe is prepared by PCR, the primer used for the PCR is designed to include complementary nucleotide sequences of the capture oligonucleotides and positive control capture oligonucleotide. It should be noted here that the probe may be longer than or shorter than the capture oligonucleotide or positive control capture oligonucleotide, so long as it allows for hybridization. In order to obtain the labeling probe, the primer used for the PCR may be labeled in advance. Alternatively, the labeling probe may be obtained by labeling the PCR substrate (deoxynucleoside triphosphate). Further, the probe may be labeled after the PCR. The labeling material is not particularly limited. For example, a fluorescent material, hapten, radioactive material, and various other materials used for the probe in common hybridization techniques may be used. Specific examples of a fluorescent material include fluorescein (FITC), rodamine, phycoerythrin (PE), Texas red, and fluorescent dye. As a hapten, biotin, digoxigenin (Dig), dinitrophenyl (DNP), or fluorescein may be used, for example.

[Hybridization Step]

In the hybridization step, the labeling probe is hybridized with an oligonucleotide that is based on a nucleotide sequence specific to the species or genus to which subject bacteria belong. It is preferable that the hybridization be carried out with a bacteria detecting instrument according to the present invention, even though the method can also be carried out, for example, on an oligonucleotide-immobilized membrane. The bacteria detecting instrument allows for thorough detection and identification that is more convenient, faster, and more accurate. A method used in the hybridization step is not particularly limited, and may be suitably selected from known nucleic acid hybridization methods. One specific example of a hybridization method is described below.

The labeling probes are added to a hybridization solution containing a saline solution, a blocking solution, and an additive. Here, the saline solution may be a standard saline citrate (SSC), for example. The detergent may be sodium dodecyl sulfate (SDS), and the blocking reagent may be bovine serum albumin (BSA), for example. The additive is added to facilitate hybridization. When the probes are double stranded, they are denatured by applying heat, for example. Then, several micro liters of the labeling probe solution is dropped on the substrate, and the whole is heated for several hours (generally at 37° C. to 50° C.), so as to allow the labeling probes to hybridize with the oligonucleotides immobilized on the substrate. Thereafter, 5×SSC or 3M tetramethyl ammonium chloride is added onto the substrate, and the substrate is heated (generally at 37° C. to 50° C.) to remove labeling probes that did not form specific hybrids. As a result, only the specific hybrids selectively remain on the substrate.

[Signal Detecting Step]

In the signal detecting step, the success or failure of hybridization in the hybridization step is determined. Generally, the signal detecting step is carried out continuously after the hybridization step.

A method used in the hybrid detecting step depends on the labeling material introduced into the probe prepared in the probe preparing step. That is, for the detection of hybrids, a fluorescent material, hapten, or other labeling materials introduced into the probe is used. As such, a method of detecting a labeling substance in the probe can be suitably selected from known methods.

For example, when using a hapten, a solution containing a conjugate (enzyme conjugate) of (i) a protein that recognizes the hapten or binds to the hapten and (ii) alkali phosphatase or horseradish peroxidase is applied onto the substrate. Then, the substrate is incubated for several ten minutes at room temperature. Note that, before allowing for the bonding reaction between the hapten and enzyme conjugate, the substrate may be completely coated with a protein such as casein except for regions on which the oligonucleotides are immobilized. In this way, a non-specific absorption reaction between the enzyme conjugate and substrate can be avoided. This can be carried out by applying a solution of casein or other proteins onto the oligonucleotide-immobilized substrate, and by allowing the substrate to stand for several ten minutes at room temperature. After the completion of the bonding reaction between the enzyme conjugate and the hapten in the probe, the enzyme conjugate that did not bind to the hapten is washed away with a suitable buffer containing a surfactant. As a result, only the enzyme conjugate that formed a bond with the hapten in the probe remains on the substrate.

For the visualization of the hybrids, such a compound is added that forms an insoluble compound only when there is a conjugate of the hapten and the enzyme conjugate. The insoluble compound turns visible by being amplified by a catalytic reaction. When alkali phosphatase is used for the enzyme conjugate, nitroblue tetrazolium chloride (NBT) and BCIP (5-bromo-4-chloro-3-indolyl phosphate, p-toluidine salt) are used as the compounds. When the enzyme is horseradish peroxitase, TMB (3,3',5,5' tetramethyl benzidine) is used as the compound, for example.

Determination of bacteria species contained in the test sample is made based on the hybridization signal such as pigmentation or fluorescein of the hybrids found in places where the capture oligonucleotides are immobilized. That is, when the hybridization signal is detected, it means that the test sample contains bacteria that correspond to the oligonucleotides forming spots at places where the hybridization signal is seen. It should be noted here that the presence of a hybridization signal at places where the positive control capture oligonucleotides are immobilized means that the test is being conducted properly. The absence of a hybridization signal at the places where the negative control capture oligonucleotides are immobilized means that the hybridization was conducted under appropriate conditions.

(3) Bacteria Detecting Kit According to the Present Invention

A bacteria detecting kit according to the present invention is used to carry out a bacteria detecting method of the present invention. As such, the bacteria detecting kit is not just limited to a particular form as long as it can be used to carry out a bacteria detecting method of the present invention.

It is preferable that a bacteria detecting kit according to the present invention includes a bacteria detecting instrument of the present invention. With the bacteria detecting instrument, the bacteria detecting kit allows for thorough detection and identification that is more convenient, faster, and more accurate. It is also preferable that a bacteria detecting kit according to the present invention includes reagents used in the hybridization step and signal detecting step. Non-limiting examples of reagents used in the hybridization step include: a saline solution such as SSC (standard saline citrate); a detergent such as sodium dodecyl sulfate (SDS); a blocking reagent such as bovine serum albumin (BSA); and an additive for facilitating hybridization. Non-limiting examples of reagents used in the signal detecting step include: a conjugate (enzyme conjugate) of a hapten-recognizing protein and an enzyme; and a chromogenic substrate such as NBT, BCIP, or TMB. The reagents are suitably selected depending on intended use, and included in the kit.

It is preferable that the bacteria detecting kit includes a reagent used in the probe preparing step, and more preferably a reagent used in the nucleic acid preparing step as well. Non-limiting examples of a reagent used in the probe preparing step include: a PCR buffer; a heat-resistant DNA polymerase; and a mixture containing deoxynucleoside triphosphate. Non-limiting examples of a reagent used in the nucleic acid preparing step include: a buffer for bacteriolysis; a DNA collecting column; and a DNA extracting buffer. The reagents are suitably selected depending on intended use, and included in the kit.

With the bacteria detecting kit according to the present invention (including the bacteria detecting instrument and reagents used in the respective steps of the method), bacteria contained in a test sample can be detected and identified in about 6 hours from the receipt of the test sample.

(4) Use of the Present Invention

Use of a bacteria detecting instrument, bacteria detecting method, and bacteria detecting kit according to the present invention is not particularly limited. They can be used for any purpose requiring bacterial determination. Specifically, a bacteria detecting instrument, bacteria detecting method, and bacteria detecting kit according to the present invention are suitably used, for example, in manufacture of various industrial products where bacterial contamination has serious effects on product quality, and where quick and accurate detection and identification of bacteria separated from the products or manufacture environment, etc. are required.

Non-limiting representative examples of such industrial products from which subject bacteria are obtained include foods, beverages, medical drugs, reagents, quasi-drugs, and disposable medical instruments. Among these industrial products, the present invention is particularly suitable for foods. Specifically, non-limiting examples of foods include: bread, sweets of various kinds (including cold or frozen sweets), prepared food, dairy products, cereals, tofu, fried tofu, noodles, box lunch, seasonings, agricultural products such as wheat flour or meat, nutraceutical foods (including various supplements), and preserved food (canned food, frozen food, retort-packed food, etc.).

Among these examples, the present invention is particularly suitable for malt alcoholic beverages, non-limiting examples of which include beer and low-malt beer.

The following will describe the present invention in more detail by way of Examples. It should be noted that the present invention is not limited in any way by the following Examples.

[Synthesis of Oligonucleotides]

According to ordinary method, an oligonucleotide synthesizer (the product of Perkin-elmer Applied biosystems) was used to synthesize oligonucleotides. After deprotection, the product was dried. The dried mass of oligonucleotide was dissolved using 10 mM Tris-HCl (pH=7.5) and 1 mM EDTA buffer, so as to prepare 100 pmol/µL of oligonucleotide solution. All the oligonucleotides used in the Example were synthesized according to this procedure. The oligonucleotides had nucleotide sequences as represented by SEQ ID NOs: 1 through 72. The oligonucleotides of SEQ ID NOs: 1 through 64, 71 and 72 are capture oligonucleotides, SEQ ID NO: 65 is the positive control capture oligonucleotide for subject bacteria, SEQ ID NO: 66 is the negative control capture oligonucleotide, SEQ ID NOs: 67 and 68 are the primers, SEQ ID NO: 69 is the control probe, and SEQ ID NO: 70 is the positive control capture oligonucleotide for the control probe. For each capture oligonucleotide, an amino group was ligated to the 5' end with the synthesizer. For each primer, biotin was adapted to the 5' end.

[Spotting of Capture Oligonucleotides on a Substrate]

Ten µl of a spotting solution (TeleChem International Inc.) was mixed with a 10 µl solution containing an oligonucleotide having an amino group at the 5' end. The mixture was then placed in each well of a micro titer plate (the product of Greiner Laboratory Inc.). Then, the slide glass CarboStation for processing carbodiimido resin (the product of Nisshinbo Industries, Inc.) was set on a predetermined position of a spotting machine, and the spotting machine was operated. After the spotting, a steam of hot water was applied onto the slide glass for several seconds, followed by irradiation of 600 mJ ultraviolet light. After exposed to the steam for several more seconds, the slide glass was placed on a hot plate to remove water. Then, for blocking, the slide glass was immersed for 30 minutes at room temperature in a 3% BSA (bovine serum albumin)-containing mixture of 100 mM Tris-HCl (pH=7.5), 100 mM NaCl, and 0.1% Triton X-100, followed by washing with a 10 mM Tris-HCl (pH=7.5) and 1 mM EDTA buffer. The slide glass was then dried at room temperature and was kept in cool and dark in a dried state for later use. FIG. 1(a) shows positions of oligonucleotides immobilized on a substrate of the bacteria detecting instrument actually used in the Examples.

[Nucleic Acid Preparing Step]

For the specimens, 30 different species of bacteria were used, including 14 species of *Lactobacillus*, 5 species of *Pediococcus*, 1 species of *Streptococcus*, 1 species of *Leuconostoc*, 3 species of *Megasphera*, 2 species of *Pectinatus*, 2 species of *Zymomonas*, 1 species of *Enterococcus*, and 1 species of *Lactococcus*. Table 5 represents bacteria used as specimens.

TABLE 5

| Genus | | Genus | |
|---|---|---|---|
| Genus | Lactobacillus | Genus | Streptococcus |
| | Lactobacillus brevis | | Streptococcus alactolyticus |
| | Lactobacillus buchneri | Genus | Leuconostoc |
| | Lactobacillus lindneri | | Leuconostoc mesenteroides |
| | Lactobacillus coryniformis | Genus | Megasphaera |
| | Lactobacillus curvatus | | Megasphaera cerevisiae |
| | Lactobacillus plantarum | | Megasphaera elsdenii |
| | Lactobacillus casei | | Megasphaera micronuciformis |
| | Lactobacillus fermentum | Genus | Pectinatus |
| | Lactobacillus delbrueckii | | Pectinatus cerevisiiphilus |
| | Lactobacillus malefermentans | | Pectinatus frisingensis |
| | Lactobacillus psittaci | Genus | Zymomonas |
| | Lactobacillus sakei | | Zymomonas mobilis |
| | Lactobacillus zeae | | Zymomonas pomaceae |
| | Lactobacillus rhamnosus | Genus | Enterococcus |
| Genus | Pediococcus | | Enterococcus durans |
| | Pediococcus damnosus | Genus | Lactococcus |
| | Pediococcus acidilactici | | Lactococcus lactis |
| | Pediococcus claussenii | | |
| | Pediococcus dextrinicus | | |
| | Pediococcus urinaeequi | | |

From a bacterial culture of each species cultured under optimum culture conditions, genomic DNA of each bacteria species was prepared using the Genomic DNA Purification Kit (the product of EdgeBioSystems, Cat. No. #85171).

[Probe Preparing Step]

Using the DNA of each bacteria species as a template, a probe nucleic acid was prepared by PCR. The reaction mixture of PCR contained 1 unit of Taq polymerase; biotinylated primers (SEQ ID NOs: 68 and 69), 10 pmol each; 5 µl of a reaction buffer (10×); dNTP, 10 nmol each; and 100 ng of template DNA. The reaction mixture had a total volume of 50 µl with the addition of sterilized distilled water. The mixture was maintained for 3 minutes at 95° C. with a thermal cycler, and the reaction was carried out in 30 cycles at 95° C. for 30 seconds, at 55° C. for 15 seconds, and at 72° C. for 1 minute. The mixture was then maintained at 72° C. for 5 minutes to finish the reaction.

Meanwhile, a synthetic sequence (control probe) was prepared that differed from the sequence of the subject bacteria except for the primer sequence. Using such a control probe as a template, PCR was carried out to prepare a biotinylated control probe. The reaction mixture of PCR had the same composition as above except that 1 ng of template DNA was used. Further, the reaction was carried out at the same reaction temperatures and in the same cycles. Without purifying the probe, the reaction mixture was directly used as a probe solution in a later hybridization step.

[Hybridization Step and Signal Detecting Step]

Three µl of the probe nucleic acid solution was mixed with 1 µl of a biotinylation control probe solution and 16 µl of an ArrayIT Unihyb Hybridization Solution (the product of TeleChem International Inc.). The mixture was heated for 1 minute at 100° C., and placed in ice for 5 minutes. A total amount of the probe nucleic acid solution was then placed on the oligonucleotide-immobilized substrate, and a cover glass was placed thereon. Then, the substrate was placed in a moisturizing container, and allowed to stand for 120 minutes in an incubator maintained at 37° C. Out of the incubator, the substrate was immediately immersed in a 2×SSC solution (2×SSC: 0.033 M NaCl, 0.033 M sodium citrate) at room temperature. With the cover glass removed, the substrate was immersed in the 2×SSC solution for 5 minutes at a maintained temperature of 37° C.

Out of the 2×SSC solution, the substrate was set in a centrifuge (the product of Beckman), and centrifuged for 1 minute at 2,000 rpm. Thereafter, 1.4 mL of an avidin-biotinylation peroxidase conjugate prepared by using the VECTASTAIN Elite ABC kit (VECTOR) was dropped on the substrate, and the substrate was allowed to stand for 30 minutes at room temperature, followed by washing in PBS (10 mM sodium phosphate (pH=7.5), and 0.9% sodium chloride). Thereafter, 1.4 mL of a chromogenic solution prepared by using the TMB substrate kit for peroxidase (VECTOR) was dropped on the substrate, and the substrate was allowed to stand for 30 minutes at room temperature. The substrate was then washed with distilled water to stop the chromogenic reaction.

[Determination]

The hybridized region was scanned at 600 dpi using the EPSON scanner GT-8700F with its transmission unit. The presence or absence of a signal was confirmed by visual inspection of the scanned image. As an example, FIG. 1($b$) depicts a scanned image for *Lactobacillus brevis*. FIG. 1($a$) shows positions of oligonucleotides on the substrate.

[Results]

Tables 6 through 35 represent results for the 30 species of bacteria used as specimens. In the tables, "O" denotes spots that exhibited a signal, and "–" denotes spots that did not exhibit a signal. As is clear from Tables 6 to 35, in the control probe, the positive control capture oligonucleotide (SEQ ID NO: 70) exhibited a signal, while no signal was observed in the negative control capture oligonucleotide. It was therefore confirmed that the amplification and hybridization were both functional. Further, for all species of bacteria, the positive control capture oligonucleotide (SEQ ID NO: 65) exhibited a signal. From this, it was confirmed that the nucleic acid prepared from each species of bacteria was actually amplified. Note that, the discussions below disregard development of a signal in the positive control capture oligonucleotides (SEQ ID NOs: 65 and 70).

Table 6 shows the result for *Lactobacillus brevis*. In *Lactobacillus brevis*, a signal was observed at 5 locations: one from the capture oligonucleotide for detecting *Lactobacillus* (SEQ ID NO: 1); and four from the capture oligonucleotides for detecting *Lactobacillus brevis* (SEQ ID NOs: 7, 8, 9, 71) (see FIGS. 1($a$) and 1($b$)). In *Lactobacillus curvatus* (Table 8), a signal was observed only at three locations: one from the capture oligonucleotide for detecting *Lactobacillus* (SEQ ID NO: 5); and two from the capture oligonucleotides for detecting *Lactobacillus curvatus* (SEQ ID NOs: 13, 14). In *Lactobacillus coryniformis* (Table 7), *Lactobacillus delbrueckii* (Table 9), *Lactobacillus lindneri* (Table 11), and *Lactobacillus malefermentans* (Table 12), a signal was observed at 4 locations in each of these bacterial species: one from the six capture oligonucleotides for detecting *Lactobacillus* (SEQ ID NOs: 1 through 6); and three from the capture oligonucleotides specific to the each species.

In *Lactobacillus fermentum* (Table 10), a signal was observed at 5 locations: one from the capture oligonucleotide for detecting *Lactobacillus* (SEQ ID NO: 6); one from the capture oligonucleotide for detecting part of *Leuconostoc* and part of *Lactobacillus* (SEQ ID NO: 72); and three from the capture oligonucleotides for detecting *Lactobacillus fermentum* (SEQ ID NOs: 19 through 21). In *Lactobacillus casei* (Table 13), a signal was observed at 4 locations: two from the capture oligonucleotides for detecting *Lactobacillus* (SEQ ID NOs: 3, 4); and two from the capture oligonucleotides for detecting *Lactobacillus casei* (SEQ ID NOs: 28, 29). In *Lactobacillus rhamnosus* (Table 14), a signal was observed at 4 locations: two from the capture oligonucleotides for detecting *Lactobacillus* (SEQ ID NOs: 3, 4); and two from the capture oligonucleotides for detecting *Lactobacillus rhamnosus* (SEQ ID NOs: 32, 33). In *Lactobacillus buchneri* (Table 15), a signal was observed at 3 locations: one from the capture oligonucleotides for detecting *Lactobacillus* (SEQ ID NO: 1); and two from the capture oligonucleotides for detecting *Lactobacillus buchneri* (SEQ ID NOs: 34, 35). In *Lactobacillus zeae* (Table 19), a signal was observed only at 4 locations: two from the capture oligonucleotides for detecting *Lactobacillus* (SEQ ID NOs: 3, 4); and two from the capture oligonucleotides for detecting *Lactobacillus zeae* (SEQ ID NOs: 30, 31).

In *Lactobacillus plantarum* (Table 16) and *Lactobacillus sakei* (Table 18), for which no species-specific capture oligonucleotides were prepared, a signal was observed at only one location from the six capture oligonucleotides for detecting *Lactobacillus*. In *Lactobacillus psittaci* (Table 17), a signal was observed at two locations: one from the capture oligonucleotide for detecting *Lactobacillus* (SEQ ID NO: 6); and one from the capture oligonucleotide for detecting part of *Leuconostoc* and part of *Lactobacillus* (SEQ ID NO: 72).

In *Pediococcus damnosus* (Table 20), *Pediococcus acidilactici* (Table 21), *Pediococcus claussenii* (Table 22), *Pediococcus dextrinicus* (Table 23), and *Pediococcus urinaeequi*

(Table 24), a signal was observed at two locations: two from the ten capture oligonucleotides for detecting *Pediococcus* (SEQ ID NOs: 36 through 45).

In *Streptococcus alactolyticus* (Table 25), a signal was observed at two locations: two from the capture oligonucleotides for detecting *Streptococcus* (SEQ ID NOs: 46, 47).

In *Leuconostoc mesenteroides* (Table 26), a signal was observed at three locations: two from the capture oligonucleotides for detecting *Leuconostoc* (SEQ ID NOs: 48, 49); and one from the capture oligonucleotide for detecting part of Leuconostoc and part of *Lactobacillus* (SEQ ID NO: 72).

In *Megasphaera cerecisiae* (Table 27), *Megasphaera elsdenii* (Table 28), and *Megasphaera micronuciformis* (Table 29), a signal was observed at two locations: two from the six capture oligonucleotides for detecting *Megasphaera* (SEQ ID NOs: 50 through 55).

In *Pectinatus cerevisiiphils* (Table 30) and *Pectinatus frisingensis* (Table 31), a signal was observed at two locations: two of the three capture oligonucleotides for detecting *Pectinatus* (SEQ ID NOs: 56 through 58).

In *Zymomonas mobilis* (Table 32) and *Zymomonas pomaceae* (Table 33), a signal was observed at two locations: two from the capture oligonucleotides for detecting *Zymomonas* (SEQ ID NOs: 59, 60).

In *Enterococcus durans* (Table 34), a signal was observed at two locations: two from the capture oligonucleotides for detecting *Enterococcus durans* (SEQ ID NOs: 61, 62).

In *Lactococcus lactis* (Table 35), a signal was observed at two locations: two from the capture oligonucleotides for detecting *Lactococcus lactis* (SEQ ID NOs: 63, 64).

As suggested by the results from each different species of tested bacteria, a signal was observed only in those spots in which species-specific capture oligonucleotides were immobilized, and a non-specific signal was not observed at all. It was therefore confirmed that the bacteria detecting instrument prepared in the Examples was usable for the genus-specific detection of *Lactobacillus, Pediococcus, Streptococcus, Leuconostoc, Megasphaera, Pectinatus*, and *Zymomonas*, and also for the species-specific detection of *Lactobacillus brevis, Lactobacillus coryniformis, Lactobacillus curvatus, Lactobacillus delbrueckii, Lactobacillus fermentum, Lactobacillus lindneri, Lactobacillus malefermentans, Lactobacillus casei* (including *Lactobacillus paracasei*), *Lactobacillus rhamnosus, Lactobacillus buchneri, Lactobacillus zeae* (including a type strain of *Lactobacillus casei*), *Enterococcus durans*, and *Lactococcus lactis*.

TABLE 6

Subject bacteria: *Lactobacillus brevis*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 o | 2 — | 3 — | |
| | 4 — | 5 — | 6 — | |
| *Lactobacillus brevis* | 7 o | 8 o | 9 o | 71 o |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |

TABLE 6-continued

Subject bacteria: *Lactobacillus brevis*

| Name of tested bacteria | SEQ ID NO: "o" = with signal, "—" = w/o signal | | | |
|---|---|---|---|---|
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of Genus *Leuconostoc* and part of Genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 7

Subject bacteria: *Lactobacillus coryniformis*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 o | 5 — | 6 — | |
| *Lactobacillus brevis* | 7 — | 8 — | 9 — | 71 — |
| *Lactobacillus coryniformis* | 10 o | 11 o | 12 o | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 8

Subject bacteria: *Lactobacillus curvatus*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 o | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 o | 14 o | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |

TABLE 8-continued

Subject bacteria: *Lactobacillus curvatus*

| Name of tested bacteria | SEQ ID NO: "o" = with signal, "—" = w/o signal | | | |
|---|---|---|---|---|
| Lactobacillus rhamnosus | 32 — | 33 — | | |
| Lactobacillus buchneri | 34 — | 35 — | | |
| Genus Pediococcus | 36 — | 37 — | 38 — | |
| | 39 — | 40 — | 41 — | |
| | 42 — | 43 — | 44 — | 45 — |
| Genus Streptococcus | 46 — | 47 — | | |
| Part of genus Leuconostoc and part of genus Lactobacillus | 48 — | 49 — | 72 — | |
| Genus Megasphaera | 50 — | 51 — | 52 — | |
| | 53 — | 54 — | 55 — | |
| Genus Pectinatus | 56 — | 57 — | 58 — | |
| Genus Zymomonas | 59 — | 60 — | | |
| Enterococcus durans | 61 — | 62 — | | |
| Lactococcus lactis | 63 — | 64 — | | |

TABLE 9

Subject bacteria: *Lactobacillus delbrueckii*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus Lactobacillus | 1 — | 2 o | 3 — | |
| | 4 — | 5 — | 6 — | |
| Lactobacillus brevis | 7 — | 8 — | 9 — | 71 — |
| Lactobacillus coryniformis | 10 — | 11 — | 12 — | |
| Lactobacillus curvatus | 13 — | 14 — | | |
| Lactobacillus delbrueckii | 16 o | 17 o | 18 o | |
| Lactobacillus fermentum | 19 — | 20 — | 21 — | |
| Lactobacillus lindneri | 22 — | 23 — | 24 — | |
| Lactobacillus malefermentans | 25 — | 26 — | 27 — | |
| Lactobacillus casei, Lactobacillus zeae | 28 — | 29 — | 30 — | 31 — |
| Lactobacillus rhamnosus | 32 — | 33 — | | |
| Lactobacillus buchneri | 34 — | 35 — | | |
| Genus Pediococcus | 36 — | 37 — | 38 — | |
| | 39 — | 40 — | 41 — | |
| | 42 — | 43 — | 44 — | 45 — |
| Genus Streptococcus | 46 — | 47 — | | |
| Part of genus Leuconostoc and part of genus Lactobacillus | 48 — | 49 — | 72 — | |
| Genus Megasphaera | 50 — | 51 — | 52 — | |
| | 53 — | 54 — | 55 — | |
| Genus Pectinatus | 56 — | 57 — | 58 — | |
| Genus Zymomonas | 59 — | 60 — | | |
| Enterococcus durans | 61 — | 62 — | | |
| Lactococcus lactis | 63 — | 64 — | | |

TABLE 10

Subject bacteria: *Lactobacillus fermentum*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus Lactobacillus | 1 — | 2 — | 3 — | |
| | 4 — | 5 — | 6 o | |
| Lactobacillus brevis | 7 — | 8 — | 9 — | 71 — |
| Lactobacillus coryniformis | 10 — | 11 — | 12 — | |
| Lactobacillus curvatus | 13 — | 14 — | | |
| Lactobacillus delbrueckii | 16 — | 17 — | 18 — | |
| Lactobacillus fermentum | 19 o | 20 o | 21 o | |
| Lactobacillus lindneri | 22 — | 23 — | 24 — | |

TABLE 10-continued

Subject bacteria: *Lactobacillus fermentum*

| Name of tested bacteria | SEQ ID NO: "o" = with signal, "—" = w/o signal | | | |
|---|---|---|---|---|
| Lactobacillus malefermentans | 25 — | 26 — | 27 — | |
| Lactobacillus casei, Lactobacillus zeae | 28 — | 29 — | 30 — | 31 — |
| Lactobacillus rhamnosus | 32 — | 33 — | | |
| Lactobacillus buchneri | 34 — | 35 — | | |
| Genus Pediococcus | 36 — | 37 — | 38 — | |
| | 39 — | 40 — | 41 — | |
| | 42 — | 43 — | 44 — | 45 — |
| Genus Streptococcus | 46 — | 47 — | | |
| Part of genus Leuconostoc and part of genus Lactobacillus | 48 — | 49 — | 72 o | |
| Genus Megasphaera | 50 — | 51 — | 52 — | |
| | 53 — | 54 — | 55 — | |
| Genus Pectinatus | 56 — | 57 — | 58 — | |
| Genus Zymomonas | 59 — | 60 — | | |
| Enterococcus durans | 61 — | 62 — | | |
| Lactococcus lactis | 63 — | 64 — | | |

TABLE 11

Subject bacteria: *Lactobacillus lindneri*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus Lactobacillus | 1 o | 2 — | 3 — | |
| | 4 — | 5 — | 6 — | |
| Lactobacillus brevis | 7 — | 8 — | 9 — | 71 — |
| Lactobacillus coryniformis | 10 — | 11 — | 12 — | |
| Lactobacillus curvatus | 13 — | 14 — | | |
| Lactobacillus delbrueckii | 16 — | 17 — | 18 — | |
| Lactobacillus fermentum | 19 — | 20 — | 21 — | |
| Lactobacillus lindneri | 22 o | 23 o | 24 o | |
| Lactobacillus malefermentans | 25 — | 26 — | 27 — | |
| Lactobacillus casei, Lactobacillus zeae | 28 — | 29 — | 30 — | 31 — |
| Lactobcillus rhamnosus | 32 — | 33 — | | |
| Lactobacillus buchneri | 34 — | 35 — | | |
| Genus Pediococcus | 36 — | 37 — | 38 — | |
| | 39 — | 40 — | 41 — | |
| | 42 — | 43 — | 44 — | 45 — |
| Genus Streptococcus | 46 — | 47 — | | |
| Part of genus Leuconostoc and part of genus Lactobacillus | 48 — | 49 — | 72 — | |
| Genus Megasphaera | 50 — | 51 — | 52 — | |
| | 53 — | 54 — | 55 — | |
| Genus Pectinatus | 56 — | 57 — | 58 — | |
| Genus Zymomonas | 59 — | 60 — | | |
| Enterococcus durans | 61 — | 62 — | | |
| Lactococcus lactis | 63 — | 64 — | | |

TABLE 12

Subject bacteria: *Lactobacillus malefermentans*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus Lactobacillus | 1 o | 2 — | 3 — | |
| | 4 — | 5 — | 6 — | |
| Lactobacillus brevis | 7 — | 8 — | 9 — | 71 — |
| Lactobacillus coryniformis | 10 — | 11 — | 12 — | |
| Lactobacillus curvatus | 13 — | 14 — | | |
| Lactobacillus delbrueckii | 16 — | 17 — | 18 — | |
| Lactobacillus fermentum | 19 — | 20 — | 21 — | |

TABLE 12-continued

Subject bacteria: *Lactobacillus malefermentans*

| Name of tested bacteria | SEQ ID NO: "o" = with signal, "—" = w/o signal | | | | | | | | |
|---|---|---|---|---|---|---|---|---|---|
| *Lactobacillus lindneri* | 22 | — | 23 | — | 24 | — | | | |
| *Lactobacillus malefermentans* | 25 | o | 26 | o | 27 | o | | | |
| *Lactobacillus casei, Lactobacillus zeae* | 28 | — | 29 | — | 30 | — | 31 | — | |
| *Lactobacillus rhamnosus* | 32 | — | 33 | — | | | | | |
| *Lactobacillus buchneri* | 34 | — | 35 | — | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | — | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 13

Subject bacteria: *Lactobacillus casei*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | — | 2 | — | 3 | o | | | |
| | 4 | o | 5 | — | 6 | — | | | |
| *Lactobacillus brevis* | 7 | — | 8 | — | 9 | — | 71 | — | |
| *Lactobacillus coryniformis* | 10 | — | 11 | — | 12 | — | | | |
| *Lactobacillus curvatus* | 13 | — | 14 | — | | | | | |
| *Lactobacillus delbrueckii* | 16 | — | 17 | — | 18 | — | | | |
| *Lactobacillus fermentum* | 19 | — | 20 | — | 21 | — | | | |
| *Lactobacillus lindneri* | 22 | — | 23 | — | 24 | — | | | |
| *Lactobacillus malefermentans* | 25 | — | 26 | — | 27 | — | | | |
| *Lactobacillus casei, Lactobacillus zeae* | 28 | o | 29 | o | 30 | — | 31 | — | |
| *Lactobacillus rhamnosus* | 32 | — | 33 | — | | | | | |
| *Lactobacillus buchneri* | 34 | — | 35 | — | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | — | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 14

Subject bacteria: *Lactobacillus rhamnosus*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | — | 2 | — | 3 | o | | | |
| | 4 | o | 5 | — | 6 | — | | | |
| *Lactobacillus brevis* | 7 | — | 8 | — | 9 | — | 71 | — | |
| *Lactobacillus coryniformis* | 10 | — | 11 | — | 12 | — | | | |
| *Lactobacillus curvatus* | 13 | — | 14 | — | | | | | |
| *Lactobacillus delbrueckii* | 16 | — | 17 | — | 18 | — | | | |

TABLE 14-continued

Subject bacteria: *Lactobacillus rhamnosus*

| Name of tested bacteria | SEQ ID NO: "o" = with signal, "—" = w/o signal | | | | | | | | |
|---|---|---|---|---|---|---|---|---|---|
| *Lactobacillus fermentum* | 19 | — | 20 | — | 21 | — | | | |
| *Lactobacillus lindneri* | 22 | — | 23 | — | 24 | — | | | |
| *Lactobacillus malefermentans* | 25 | — | 26 | — | 27 | — | | | |
| *Lactobacillus casei, Lactobacillus zeae* | 28 | — | 29 | — | 30 | — | 31 | — | |
| *Lactobacillus rhamnosus* | 32 | o | 33 | o | | | | | |
| *Lactobacillus buchneri* | 34 | — | 35 | — | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | — | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 15

Subject bacteria: *Lactobacillus buchneri*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | o | 2 | — | 3 | — | | | |
| | 4 | — | 5 | — | 6 | — | | | |
| *Lactobacillus brevis* | 7 | — | 8 | — | 9 | — | 71 | — | |
| *Lactobacillus coryniformis* | 10 | — | 11 | — | 12 | — | | | |
| *Lactobacillus curvatus* | 13 | — | 14 | — | | | | | |
| *Lactobacillus delbrueckii* | 16 | — | 17 | — | 18 | — | | | |
| *Lactobacillus fermentum* | 19 | — | 20 | — | 21 | — | | | |
| *Lactobacillus lindneri* | 22 | — | 23 | — | 24 | — | | | |
| *Lactobacillus malefermentans* | 25 | — | 26 | — | 27 | — | | | |
| *Lactobacillus casei, Lactobacillus zeae* | 28 | — | 29 | — | 30 | — | 31 | — | |
| *Lactobacillus rhamnosus* | 32 | — | 33 | — | | | | | |
| *Lactobacillus buchneri* | 34 | o | 35 | o | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | — | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 16

Subject bacteria: *Lactobacillus plantarum*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | o | 2 | — | 3 | — | | | |
| | 4 | — | 5 | — | 6 | — | | | |
| *Lactobacillus brevis* | 7 | — | 8 | — | 9 | — | 71 | — | |
| *Lactobacillus coryniformis* | 10 | — | 11 | — | 12 | — | | | |
| *Lactobacillus curvatus* | 13 | — | 14 | — | | | | | |

TABLE 16-continued

Subject bacteria: *Lactobacillus plantarum*

| Name of tested bacteria | SEQ ID NO: "o" = with signal, "—" = w/o signal | | | | | | | | |
|---|---|---|---|---|---|---|---|---|---|
| *Lactobacillus delbrueckii* | 16 | — | 17 | — | 18 | — | | | |
| *Lactobacillus fermentum* | 19 | — | 20 | — | 21 | — | | | |
| *Lactobacillus lindneri* | 22 | — | 23 | — | 24 | — | | | |
| *Lactobacillus malefermentans* | 25 | — | 26 | — | 27 | — | | | |
| *Lactobacillus casei, Lactobacillus zeae* | 28 | — | 29 | — | 30 | — | 31 | — | |
| *Lactobacillus rhamnosus* | 32 | — | 33 | — | | | | | |
| *Lactabacillus buchneri* | 34 | — | 35 | — | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | — | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 17

Subject bacteria: *Lactobacillus psittaci*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | — | 2 | — | 3 | — | | | |
| | 4 | — | 5 | — | 6 | o | | | |
| *Lactobacillus brevis* | 7 | — | 8 | — | 9 | — | 71 | — | |
| *Lactobacillus coryniformis* | 10 | — | 11 | — | 12 | — | | | |
| *Lactobacillus curvatus* | 13 | — | 14 | — | | | | | |
| *Lactobacillus delbrueckii* | 16 | — | 17 | — | 18 | — | | | |
| *Lactobacillus fermentum* | 19 | — | 20 | — | 21 | — | | | |
| *Lactobacillus lindneri* | 22 | — | 23 | — | 24 | — | | | |
| *Lactobacillus malefermentans* | 25 | — | 26 | — | 27 | — | | | |
| *Lactobacillus casei, Lactobacillus zeae* | 28 | — | 29 | — | 30 | — | 31 | — | |
| *Lactobacillus rhamnosus* | 32 | — | 33 | — | | | | | |
| *Lactobacillus buchneri* | 34 | — | 35 | — | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | o | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 18

Subject bacteria: *Lactobacillus sakei*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | — | 2 | — | 3 | — | | | |
| | 4 | — | 5 | o | 6 | — | | | |
| *Lactobacillus brevis* | 7 | — | 8 | — | 9 | — | 71 | — | |
| *Lactobacillus coryniformis* | 10 | — | 11 | — | 12 | — | | | |

TABLE 18-continued

Subject bacteria: *Lactobacillus sakei*

| Name of tested bacteria | SEQ ID NO: "o" = with signal, "—" = w/o signal | | | | | | | | |
|---|---|---|---|---|---|---|---|---|---|
| *Lactobacillus curvatus* | 13 | — | 14 | — | | | | | |
| *Lactobacillus delbrueckii* | 16 | — | 17 | — | 18 | — | | | |
| *Lactobacillus fermentum* | 19 | — | 20 | — | 21 | — | | | |
| *Lactobacillus lindneri* | 22 | — | 23 | — | 24 | — | | | |
| *Lactobacillus malefermentans* | 25 | — | 26 | — | 27 | — | | | |
| *Lactobacillus casei, Lactobacillus zeae* | 28 | — | 29 | — | 30 | — | 31 | — | |
| *Lactobacillus rhamnosus* | 32 | — | 33 | — | | | | | |
| *Lactobacillus buchneri* | 34 | — | 35 | — | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | — | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 19

Subject bacteria: *Lactobacillus zeae*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | — | 2 | — | 3 | o | | | |
| | 4 | o | 5 | — | 6 | — | | | |
| *Lactobacillus brevis* | 7 | — | 8 | — | 9 | — | 71 | — | |
| *Lactobacillus coryniformis* | 10 | — | 11 | — | 12 | — | | | |
| *Lactobacillus curvatus* | 13 | — | 14 | — | | | | | |
| *Lactobacillus delbrueckii* | 16 | — | 17 | — | 18 | — | | | |
| *Lactobacillus fermentum* | 19 | — | 20 | — | 21 | — | | | |
| *Lactobacillus lindneri* | 22 | — | 23 | — | 24 | — | | | |
| *Lactobacillus malefermentans* | 25 | — | 26 | — | 27 | — | | | |
| *Lactobacillus casei, Lactobacillus zeae* | 28 | — | 29 | — | 30 | o | 31 | o | |
| *Lactobacillus rhamnosus* | 32 | — | 33 | — | | | | | |
| *Lactobacillus buchneri* | 34 | — | 35 | — | | | | | |
| Genus *Pediococcus* | 36 | — | 37 | — | 38 | — | | | |
| | 39 | — | 40 | — | 41 | — | | | |
| | 42 | — | 43 | — | 44 | — | 45 | — | |
| Genus *Streptococcus* | 46 | — | 47 | — | | | | | |
| Part of genus *Leuconostoc* and Part of genus *Lactobacillus* | 48 | — | 49 | — | 72 | — | | | |
| Genus *Megasphaera* | 50 | — | 51 | — | 52 | — | | | |
| | 53 | — | 54 | — | 55 | — | | | |
| Genus *Pectinatus* | 56 | — | 57 | — | 58 | — | | | |
| Genus *Zymomonas* | 59 | — | 60 | — | | | | | |
| *Enterococcus durans* | 61 | — | 62 | — | | | | | |
| *Lactococcus lactis* | 63 | — | 64 | — | | | | | |

TABLE 20

Subject bacteria: *Pediococcus damnosus*

| Name of tested bacteria | SEQ ID NO: "o" = with signal, "—" = w/o signal | | | | | | | | |
|---|---|---|---|---|---|---|---|---|---|
| Positive control | 65 | o | 70 | o | | | | | |
| Negative control | 66 | — | | | | | | | |
| Genus *Lactobacillus* | 1 | — | 2 | — | 3 | — | | | |
| | 4 | — | 5 | — | 6 | — | | | |
| *Lactobacillus brevis* | 7 | — | 8 | — | 9 | — | 71 | — | |

TABLE 20-continued

Subject bacteria: *Pediococcus damnosus*

| Name of tested bacteria | SEQ ID NO: "o" = with signal, "—" = w/o signal | | | | | | | |
|---|---|---|---|---|---|---|---|---|
| *Lactobacillus coryniformis* | 10 | — | 11 | — | 12 | — | | |
| *Lactobacillus curvatus* | 13 | — | 14 | — | | | | |
| *Lactobacillus delbrueckii* | 16 | — | 17 | — | 18 | — | | |
| *Lactobacillus fermentum* | 19 | — | 20 | — | 21 | — | | |
| *Lactobacillus lindneri* | 22 | — | 23 | — | 24 | — | | |
| *Lactobacillus malefermentans* | 25 | — | 26 | — | 27 | — | | |
| *Lactobacillus casei*, *Lactobacillus zeae* | 28 | — | 29 | — | 30 | — | 31 | — |
| *Lactobacillus rhamnosus* | 32 | — | 33 | — | | | | |
| *Lactobacillus buchneri* | 34 | — | 35 | — | | | | |
| Genus *Pediococcus* | 36 | o | 37 | — | 38 | — | | |
| | 39 | — | 40 | — | 41 | o | | |
| | 42 | — | 43 | — | 44 | — | 45 | — |
| Genus *Streptococcus* | 46 | — | 47 | — | | | | |
| Part of genus *Leuconostoc* and Part of genus *Lactobacillus* | 48 | — | 49 | — | 72 | — | | |
| Genus *Megasphaera* | 50 | — | 51 | — | 52 | — | | |
| | 53 | — | 54 | — | 55 | — | | |
| Genus *Pectinatus* | 56 | — | 57 | — | 58 | — | | |
| Genus *Zymomonas* | 59 | — | 60 | — | | | | |
| *Enterococcus durans* | 61 | — | 62 | — | | | | |
| *Lactococcus lactis* | 63 | — | 64 | — | | | | |

TABLE 21

Subject bacteria: *Pediococcus acidilactici*

| Name of tested bacteria | SEQ ID NO: "o" = with signal, "—" = w/o signal | | | | | | | |
|---|---|---|---|---|---|---|---|---|
| Positive control | 65 | o | 70 | o | | | | |
| Negative control | 66 | — | | | | | | |
| Genus *Lactobacillus* | 1 | — | 2 | — | 3 | — | | |
| | 4 | — | 5 | — | 6 | — | | |
| *Lactobacillus brevis* | 7 | — | 8 | — | 9 | — | 71 | — |
| *Lactobacillus coryniformis* | 10 | — | 11 | — | 12 | — | | |
| *Lactobacillus curvatus* | 13 | — | 14 | — | | | | |
| *Lactobacillus delbrueckii* | 16 | — | 17 | — | 18 | — | | |
| *Lactobacillus fermentum* | 19 | — | 20 | — | 21 | — | | |
| *Lactobacillus lindneri* | 22 | — | 23 | — | 24 | — | | |
| *Lactobacillus malefermentans* | 25 | — | 26 | — | 27 | — | | |
| *Lactobacillus casei*, *Lactobacillus zeae* | 28 | — | 29 | — | 30 | — | 31 | — |
| *Lactobacillus rhamnosus* | 32 | — | 33 | — | | | | |
| *Lactobacillus buchneri* | 34 | — | 35 | — | | | | |
| Genus *Pediococcus* | 36 | — | 37 | o | 38 | — | | |
| | 39 | — | 40 | — | 41 | — | | |
| | 42 | o | 43 | — | 44 | — | 45 | — |
| Genus *Streptococcus* | 46 | — | 47 | — | | | | |
| Part of genus *Leuconostoc* and part of genus *Lactobacillus* | 48 | — | 49 | — | 72 | — | | |
| Genus *Megasphaera* | 50 | — | 51 | — | 52 | — | | |
| | 53 | — | 54 | — | 55 | — | | |
| Genus *Pectinatus* | 56 | — | 57 | — | 58 | — | | |
| Genus *Zymomonas* | 59 | — | 60 | — | | | | |
| *Enterococcus durans* | 61 | — | 62 | — | | | | |
| *Lactococcus lactis* | 63 | — | 64 | — | | | | |

TABLE 22

Subject bacteria: *Pediococcus claussenii*

| Name of tested bacteria | SEQ ID NO: "o" = with signal, "—" = w/o signal | | | | | | | |
|---|---|---|---|---|---|---|---|---|
| Positive control | 65 | o | 70 | o | | | | |
| Negative control | 66 | — | | | | | | |

TABLE 22-continued

Subject bacteria: *Pediococcus claussenii*

| Name of tested bacteria | SEQ ID NO: "o" = with signal, "—" = w/o signal | | | | | | | |
|---|---|---|---|---|---|---|---|---|
| Genus *Lactobacillus* | 1 | — | 2 | — | 3 | — | | |
| | 4 | — | 5 | — | 6 | — | | |
| *Lactobacillus brevis* | 7 | — | 8 | — | 9 | — | 71 | — |
| *Lactobacillus coryniformis* | 10 | — | 11 | — | 12 | — | | |
| *Lactobacillus curvatus* | 13 | — | 14 | — | | | | |
| *Lactobacillus delbrueckii* | 16 | — | 17 | — | 18 | — | | |
| *Lactobacillus fermentum* | 19 | — | 20 | — | 21 | — | | |
| *Lactobacillus lindneri* | 22 | — | 23 | — | 24 | — | | |
| *Lactobacillus malefermentans* | 25 | — | 26 | — | 27 | — | | |
| *Lactobacillus casei*, *Lactobacillus zeae* | 28 | — | 29 | — | 30 | — | 31 | — |
| *Lactobacillus rhamnosus* | 32 | — | 33 | — | | | | |
| *Lactobacillus buchneri* | 34 | — | 35 | — | | | | |
| Genus *Pediococcus* | 36 | — | 37 | — | 38 | — | | |
| | 39 | — | 40 | o | 41 | — | | |
| | 42 | o | 43 | o | 44 | — | 45 | — |
| Genus *Streptococcus* | 46 | — | 47 | — | | | | |
| Part of genus *Leuconostoc* and part of genus *Lactobacillus* | 48 | — | 49 | — | 72 | — | | |
| Genus *Megasphaera* | 50 | — | 51 | — | 52 | — | | |
| | 53 | — | 54 | — | 55 | — | | |
| Genus *Pectinatus* | 56 | — | 57 | — | 58 | — | | |
| Genus *Zymomonas* | 59 | — | 60 | — | | | | |
| *Enterococcus durans* | 61 | — | 62 | — | | | | |
| *Lactococcus lactis* | 63 | — | 64 | — | | | | |

TABLE 23

Subject bacteria: *Pediococcus dextrinicus*

| Name of tested bacteria | SEQ ID NO: "o" = with signal, "—" = w/o signal | | | | | | | |
|---|---|---|---|---|---|---|---|---|
| Positive control | 65 | o | 70 | o | | | | |
| Negative control | 66 | — | | | | | | |
| Genus *Lactobacillus* | 1 | — | 2 | — | 3 | — | | |
| | 4 | — | 5 | — | 6 | — | | |
| *Lactobacillus brevis* | 7 | — | 8 | — | 9 | — | 71 | — |
| *Lactobacillus coryniformis* | 10 | — | 11 | — | 12 | — | | |
| *Lactobacillus curvatus* | 13 | — | 14 | — | | | | |
| *Lactobacillus delbrueckii* | 16 | — | 17 | — | 18 | — | | |
| *Lactobacillus fermentum* | 19 | — | 20 | — | 21 | — | | |
| *Lactobacillus lindneri* | 22 | — | 23 | — | 24 | — | | |
| *Lactobacillus malefermentans* | 25 | — | 26 | — | 27 | — | | |
| *Lactobacillus casei*, *Lactobacillus zeae* | 28 | — | 29 | — | 30 | — | 31 | — |
| *Lactobacillus rhamnosus* | 32 | — | 33 | — | | | | |
| *Lactobacillus buchneri* | 34 | — | 35 | — | | | | |
| Genus *Pediococcus* | 36 | — | 37 | — | 38 | o | | |
| | 39 | — | 40 | — | 41 | — | | |
| | 42 | — | 43 | — | 44 | — | 45 | o |
| Genus *Streptococcus* | 46 | — | 47 | — | | | | |
| Part of genus *Leuconostoc* and part of genus *Lactobacillus* | 48 | — | 49 | — | 72 | — | | |
| Genus *Megasphaera* | 50 | — | 51 | — | 52 | — | | |
| | 53 | — | 54 | — | 55 | — | | |
| Genus *Pectinatus* | 56 | — | 57 | — | 58 | — | | |
| Genus *Zymomonas* | 59 | — | 60 | — | | | | |
| *Enterococcus durans* | 61 | — | 62 | — | | | | |
| *Lactococcus lactis* | 63 | — | 64 | — | | | | |

TABLE 24

Subject bacteria: *Pediococcus urinaeequi*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 o | 40 — | 41 — | |
| | 42 — | 43 — | 44 o | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 25

Subject bacteria: *Streptococcus alactolyticus*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 o | 47 o | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 26

Subject bacteria: *Leuconostoc mesenteroides*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 o | 49 o | 72 o | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 27

Subject bacteria: *Megasphaera cerevisiae*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 o | 51 — | 52 — | |
| | 53 o | 54 — | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 28

Subject bacteria: *Megasphaera elsdenii*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 o | 52 — | |
| | 53 — | 54 — | 55 o | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 29

Subject bacteria: *Megasphaera micronuciformis*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 o | |
| | 53 — | 54 o | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 30

Subject bacteria: *Pectinatus cerevisiiphilus*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 o | 57 o | 58 — | |
| Genus *Zymomonas* | 59 — | 60 — | | |
| *Enterococcus durans* | 61 — | 62 — | | |
| *Lactococcus lactis* | 63 — | 64 — | | |

TABLE 31

Subject bacteria: *Pectinatus frisingensis*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 o | 57 — | 58 o | |
| Genus *Zymomonas* | 59 — | 60 — | | |
| *Enterococcus durans* | 61 — | 62 — | | |
| *Lactococcus lactis* | 63 — | 64 — | | |

TABLE 32

Subject bacteria: *Zymomonas mobilis*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 o | 60 o | | |
| *Enterococcus durans* | 61 — | 62 — | | |
| *Lactococcus lactis* | 63 — | 64 — | | |

TABLE 33

Subject bacteria: *Zymomonas pomaceae*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 o | 60 o | | |
| *Enterococcus durans* | 61 — | 62 — | | |
| *Lactococcus lactis* | 63 — | 64 — | | |

TABLE 34

Subject bacteria: *Enterococcus durans*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 — | 60 — | | |
| *Enterococcus durans* | 61 o | 62 o | | |
| *Lactococcus lactis* | 63 — | 64 — | | |

TABLE 35

Subject bacteria: *Lactococcus lactis*

| Name of tested bacteria | SEQ ID NO: "o" = with signal, "—" = w/o signal | | | |
|---|---|---|---|---|
| Positive control | 65 o | 70 o | | |
| Negative control | 66 — | | | |
| Genus *Lactobacillus* | 1 — | 2 — | 3 — | |
| | 4 — | 5 — | 6 — | |
| *Lactobacillus brevis* | 7 — | 8 — | 9 — | 71 — |
| *Lactobacillus coryniformis* | 10 — | 11 — | 12 — | |
| *Lactobacillus curvatus* | 13 — | 14 — | | |
| *Lactobacillus delbrueckii* | 16 — | 17 — | 18 — | |
| *Lactobacillus fermentum* | 19 — | 20 — | 21 — | |
| *Lactobacillus lindneri* | 22 — | 23 — | 24 — | |
| *Lactobacillus malefermentans* | 25 — | 26 — | 27 — | |
| *Lactobacillus casei, Lactobacillus zeae* | 28 — | 29 — | 30 — | 31 — |
| *Lactobacillus rhamnosus* | 32 — | 33 — | | |
| *Lactobacillus buchneri* | 34 — | 35 — | | |
| Genus *Pediococcus* | 36 — | 37 — | 38 — | |
| | 39 — | 40 — | 41 — | |
| | 42 — | 43 — | 44 — | 45 — |
| Genus *Streptococcus* | 46 — | 47 — | | |
| Part of genus *Leuconostoc* and part of genus *Lactobacillus* | 48 — | 49 — | 72 — | |
| Genus *Megasphaera* | 50 — | 51 — | 52 — | |
| | 53 — | 54 — | 55 — | |
| Genus *Pectinatus* | 56 — | 57 — | 58 — | |
| Genus *Zymomonas* | 59 — | 60 — | | |
| *Enterococcus durans* | 61 — | 62 — | | |
| *Lactococcus lactis* | 63 o | 64 o | | |

While the invention is susceptible to various modifications and alternative forms, a specific embodiment thereof will be described below in more detail by way of Examples with reference to the attached drawings. It should be understood, however, that it is not intended to limit the invention to the particular forms disclosed, but on the contrary, the invention is to cover all modifications, equivalents, and alternatives falling within the scope of the invention as defined in the appended claims.

The invention claimed is:

1. An instrument for detecting and identifying *Lactobacillus brevis* or *Lactobacillus lindneri* contained in a test sample, comprising a substrate on a surface of which are immobilized:

(1) oligonucleotides comprising a species- or genus-specific sequence of a 16S ribosomal RNA gene of *Lactobacillus brevis*, which comprise:
   (i) an oligonucleotide consisting of the nucleotide sequence of SEQ ID NO: 7;
   (ii) an oligonucleotide consisting of the nucleotide sequence of SEQ ID NO: 8;
   (iii) an oligonucleotide consisting of the nucleotide sequence of SEQ ID NO: 9; and
   (iv) an oligonucleotide consisting of the nucleotide sequence of SEQ ID NO: 71,
and (2) oligonucleotides comprising a species- or genus-specific sequence of a 16S ribosomal RNA gene of *Lactobacillus lindneri*, which comprise:
   (i) an oligonucleotide comprising consisting of the nucleotide sequence of SEQ ID NO: 22;
   (ii) an oligonucleotide consisting of the nucleotide sequence of SEQ ID NO: 23; and
   (iii) an oligonucleotide consisting of the nucleotide sequence of SEQ ID NO: 24,
wherein the bacteria contained in the test sample are detected and identified through hybridization of at least one the oligonucleotides with a nucleic acid derived from the test sample.

2. The instrument of claim 1, wherein the immobilized oligonucleotides further comprise an oligonucleotide selected from the group consisting of the nucleotide sequence of SEQ ID NOS: 1-6, 10-21, 25-64, and 72.

* * * * *